US007312052B1

(12) United States Patent
Sorge et al.

(10) Patent No.: US 7,312,052 B1
(45) Date of Patent: Dec. 25, 2007

(54) POLYMERASE COMPOSITIONS AND USES THEREOF

(75) Inventors: Joseph A. Sorge, Rancho Sante Fe, CA (US); Rebecca Lynn Mullinax, San Diego, CA (US)

(73) Assignee: Stratagene California, La Jolla, CA (US)

( * ) Notice: Subject to any disclaimer, the term of this patent is extended or adjusted under 35 U.S.C. 154(b) by 254 days.

(21) Appl. No.: 08/529,767

(22) Filed: Sep. 18, 1995

Related U.S. Application Data

(63) Continuation of application No. 08/197,791, filed on Feb. 16, 1994, now Pat. No. 5,556,772, which is a continuation-in-part of application No. 08/164,290, filed on Dec. 8, 1993, now abandoned.

(51) Int. Cl.
C12P 19/34 (2006.01)
C12Q 1/68 (2006.01)
C07H 21/02 (2006.01)

(52) U.S. Cl. .......................... 435/91.2; 435/6; 536/24.3
(58) Field of Classification Search .................... 435/6, 435/91.2, 196, 188, 194
See application file for complete search history.

(56) References Cited

U.S. PATENT DOCUMENTS

| | | | |
|---|---|---|---|
| 4,376,110 A | 3/1983 | David et al. | |
| 4,683,202 A | 7/1987 | Mullis | |
| 4,795,699 A | 1/1989 | Tabor et al. | |
| 4,800,159 A | 1/1989 | Mullis et al. | |
| 4,921,794 A | 5/1990 | Tabor et al. | |
| 4,946,786 A | 8/1990 | Tabor et al. | |
| 5,001,050 A | 3/1991 | Blanco et al. | |
| 5,075,216 A | 12/1991 | Innis et al. | |
| 5,079,352 A | 1/1992 | Gelfand et al. | |
| 5,210,036 A | 5/1993 | Comb et al. | |
| 5,310,652 A | 5/1994 | Gelfand et al. | |
| 5,322,785 A | 6/1994 | Comb et al. | |
| 5,352,778 A | 10/1994 | Comb et al. | |
| 5,352,785 A | 10/1994 | Herzberg et al. | |
| 5,374,553 A | 12/1994 | Gelfand et al. | |
| 5,422,239 A | 6/1995 | Wands et al. | |
| 5,436,149 A * | 7/1995 | Barnes ........................... 435/6 |
| 5,466,591 A | 11/1995 | Abramson et al. | |
| 5,489,523 A | 2/1996 | Mathur | |
| 5,500,363 A | 3/1996 | Comb et al. | |
| 5,512,462 A * | 4/1996 | Cheng ........................ 435/91.2 |
| 5,545,552 A | 8/1996 | Mathur | |
| 5,556,772 A | 9/1996 | Sorge et al. | |
| 5,618,702 A | 4/1997 | Scanlon | |
| 6,410,277 B1 | 6/2002 | Barnes | |

FOREIGN PATENT DOCUMENTS

| | | |
|---|---|---|
| EP | 0 265 293 A2 | 4/1988 |
| EP | 0 386 857 A2 | 9/1990 |
| EP | 0 416 755 A1 | 3/1991 |
| EP | 502589 A2 | 9/1992 |
| WO | WO89/06691 A2 | 7/1989 |
| WO | WO91/02090 A1 | 2/1991 |
| WO | WO92/06188 A2 | 4/1992 |
| WO | WO92/06200 A1 | 4/1992 |
| WO | WO92/09689 | 6/1992 |
| WO | WO 92/09689 | 6/1992 |

OTHER PUBLICATIONS

Summons, undated.
Summons in a Civil Case, undated.
Summons in a Civil Action, undated.
Plaintiff Takara Bio, Inc.'s First Amended Complaint Under the Patent Law, undated.
Notice of Motion to Dismiss, Transfer or Stay Action, with Exhibits A-V, undated.
Takara Bio, Inc.'s Memorandum of Points and Authorities in Opposition to Strategene's Motion to Dismiss, Stay or Transfer, with Declaration of John B. Pegram and Exhibits 1-4, 6, 8, 9, and 11-32, undated.
Defendant Stratagene's Reply in Support of Motion to Transfer, Dismiss or Stay, with Exhibits A and B, undated.
Order Granting Defendant's Motion to Transfer, undated.

(Continued)

*Primary Examiner*—Jeffrey Fredman

(57) ABSTRACT

The subject invention provides novel compositions containing a mixture of (a) an enzyme that possesses substantial 3'–5' exonuclease activity (b) a DNA polymerase with less 3'–5' exonuclease activity than the enzyme with substantial 3'–5' exonuclease activity. Preferably, the DNA polymerase for inclusion in the compositions are DNA polymerases that substantially lack 3'–5' exonuclease activity. A preferred embodiment of the invention is a composition comprising the Taq DNA polymerase (isolated from *Thermus aquaticus*) and the Pfu DNA polymerase (isolated from *Pyrococcus furiosus*). Another aspect of the invention is to provide methods for synthesizing polynucleotides, typically DNA, using compositions comprising an enzyme that possesses substantial 3'–5' exonuclease activity and a DNA polymerase with less 3'–5' exonuclease activity than the enzymes possessing substantial 3'–5' exonuclease activity, preferably a DNA polymerase that substantially lacks 3'–5' exonuclease activity. Another aspect of the invention involves the use the subject method of polynucleotide synthesis to carry out the synthesis step in a polymerase chain reaction experiment. Yet another aspect of the invention is to provide kits for the synthesis of polynucleotides, wherein the kits comprise an enzyme that possesses substantial 3'–5' exonuclease activity and a DNA polymerase with less 3'–5' exonuclease activity than the enzyme possessing substantial 3'–5' exonuclease activity.

39 Claims, No Drawings

OTHER PUBLICATIONS

U.S. District Court, District of Maryland (Baltimore), Civil Docket for Case #: 1:03-cv-01871-WMN, undated.
Stratagene's Answer to Plaintiff Takara Bio, Inc's First Amended Complaint Under the Patent Law, undated.
Request by Takara Bio Inc. for Leave to Participate in this Reexamination as a Partial Assignee (Co-owner) and other Takara Bio Inc. Submissions with Exhibits 1-7 and A-L, undated.
Letter Concerning Request by Takara Bio Inc. for Leave to Participate in this Reexamination as a Partial Assignee (Co-owner) and other Takara Bio Inc. Submissions, with Exhibits 1 and 2, undated.
Letter Submitting Copy of Request by Takara Bio Inc. for Leave to Participate in this Reexamination as a Partial Assignee (Co-owner) and other Takara Bio Inc. Submissions, undated.
Reply to Owner's Statement Under 37 C.F.R. § 1.535, Transmittal Form, and Certificate of Service, undated.
Barnes, W. "The fidelity of *Taq* polymerase catalyzing PCR is improved by a N-terminal deletion," Gene, 112: 29-35 (1992).
Lundberg et al. "High-fidelity amplification using a thermostable DNA polymerase isolated from *Pyrococcus furiosus*," Gene, 108: 1-6 (1991).
Ohler et al. "Optimization of Long-distance PCR using a transposon-based model system," PCR Methods and Applications, 2: 51-59 (1992).
Perrino et al., "Hydrolosis of 3'-terminal mispairs in vitro by the 3' → 5'exonuclease of DNA polymerase δ permits subsequent extension by DNA polymerase α," Biochemistry, 29: 5226-5231 (1990).
Perrino et al., "Proofreading by the ε subunit of *Escherichia coli* DNA polymerase III increases the fidelity of calf thymus DNA polymerase α," Proc. Natl. Acad. Sci. USA, 86: 3085-3088 (1989).
Tindall et al., "Fidelity of DNA synthesis by the *Thermus aquaticus* DNA polymerase." Biochemistry, 27:6008-6013 (1988).
New England BioLabs catalog on Deep Vent $DNA_R$™ Polymerase, p. 61 (1992).
New England Biolabs catalog on Deep $Vent_R$® polymerase, p. 62, submitted in Exhibit E of the Request for Reexamination Under 37 C.F.R. §1.510 (for U.S. Patent No. 5,556,772) filed by Kate Murashige on Mar. 20, 2003, and alleged to be dated 1992 in that Request for Reexamination.
The American Heritage College Dictionary, Third Edition, Houghton Mifflin Company, p. 750, submitted in Exhibit H of the Request for Reexamination Under 37 C.F.R. §1.510 (for U.S. Patent No. 5,556,772) filed by Kate Murashige on Mar. 20, 2003.
http://bio.takara.co.jp/BIO_EN/Catalog_d.asp?C_ID=C0173 (Dec. 19, 2002) (6 pages), submitted in Exhibit J of the Request for Reexamination Under 37 C.F.R. §1.510 (for U.S. Patent No. 5,556,772) filed by Kate Murashige on Mar. 20, 2003.
http://bio.takara.co.jp/BIO_EN/Catalog_d.asp?C_ID=C0174 (Dec. 19, 2002) (5 pages), submitted in Exhibit J of the Request for Reexamination Under 37 C.F.R. §1.510 (for U.S. Patent No. 5,556,772) filed by Kate Murashige on Mar. 20, 2003.
http://www.Stratagene.com/displayProduct.asp?productId=104 (Dec. 19, 2002) (2 pages), submitted in Exhibit K of the Request for Reexamination Under 37 C.F.R. §1.510 (for U.S. Patent No. 5,556,772) filed by Kate Murashige on Mar. 20, 2003.
Stratagene product information, TaqPlus® Long and TaqPlus® Precision PCR Systems (2 pages), submitted in Exhibit K of the Request for Reexamination Under 37 C.F.R. §1.510 (for U.S. Patent No. 5,556,772) filed by Kate Murashige on Mar. 20, 2003.
Declaration of Joseph A. Sorge and Rebecca L. Mullinax Under 37 C.F.R. §1.131 from U.S. Appl. No. 08/197,791, submitted in Exhibit G of the Request for Reexamination Under 37 C.F.R. §1.510 (for U.S. Patent No. 5,556,772) filed by Kate Murashige on Mar. 20, 2003.
U.S. District Court, District of Maryland (Greenbelt), Civil Docket for Case #: 8:01-cv-03566-DKC.
Civil Cover Sheet.
Complaint for Patent Infringement.
Invitrogen Corporation's Answer to Complaint for Patent Infringement and Counterclaim.
Stratagene's Answer to Invitrogen Corporation's Counter Claim.
Expert Opinion of Thomas G. Wiseman, Esq.
Expert Witness Report of John F. Witherspoon.
U.S. District Court, District of Maryland (Baltimore), Civil Docket for Case #: 1:02-cv-03603-WMN.
Complaint for Patent Infringement.
Takara's Motion to (1) Quash Service of Process; (2) Dismiss For Inadequate Service of Process, and (3) Dismiss for Lack of Personal Jurisdiction, or (4)—If This Court Has Jurisdiction—Transfer.
U.S. District Court, Southern District of California (San Diego) Civil Docket for Case #: 03-CV-742.
Complaint Under the Patent Law.
Notice of Related Case.
Notice of Party with Financial Interest [Local Rule 40.2].
Stipulation Extending Time to file a Responsive Pleading; Order.
Request for Reexamination Under 37 C.F.R. §1.510 (for U.S. Patent No. 5,556,772) filed by Kate Murashige on Mar. 20, 2003.
Exhibits A-K.
Transmittal Form.
Post card.
Fee Transmittal.
Notice of Reexamination Request Filing Date (for U.S. Patent No. 5,556,772), mailed Mar. 31, 2003.
Order Granting/Denying Request for Ex Parte Reexamination (for U.S. Patent No. 5,556,772), mailed May 22, 2003.
Decision Returning Improper Paper (for U.S. Patent No. 5,556,772), mailed Jun. 12, 2003.
Presecution history of U.S. Appl. No. 08/197,791 (now U.S. Patent No. 5,556,772).
Amendment and Response to Notice to File Missing Parts of Nonprovisional Application filed Mar. 24, 2005, in U.S. Appl. No. 10/738,917.
Office Action mailed Jun. 2, 2006, in U.S. Appl. No. 10/738,917.
Interview Summary mailed Aug. 9, 2006, in U.S. Appl. No. 10/738,917.
Preliminary Amendment and Interview Summary filed Jan. 29, 2007, in U.S. Appl. No. 11/633,814, which is a continuation of U.S. Appl. No. 10/738,917.
Office Action mailed Jan. 26, 2007, in U.S. Appl. No. 09/631,613.
Supplemental Notice of Intent to Issue *Ex Parte* Reexamination Certificate mailed Jan. 8, 2007.
Decision Dismissing and Returning Petition mailed Oct. 11, 2006.
Response filed Sep. 25, 2006.
Anonymous, "Recombinant $Vent_R$™ DNA Polymerase," *The NEB Transcript*, 3(1):4 (1991).
Barnes, "PCR amplification of up to 35-kb DNA with high fidelity and high yield from λ bacteriophage templates," *Proc. Natl. Acad. Sci. USA*, 91:2216-2220 (1994).
Cheng et al., "Effective amplification of long targets from cloned inserts and human genomic DNA," *Proc. Natl. Acad. Sci. USA*, 91:5695-5699 (1994).
Lawyer et al., "High-level expression, purification, and enzymatic characterization of full-length *Thermus aquaticus* DNA polymerase and a truncated form deficient in 5'to 3'exonuclease activity," *PCR Methods and Applications*, 2:275-287 (1993).
Lehninger et al., *Principles of Biochemistry*, $2^{nd}$ Edition, Worth Publishers, New York, NY, pp. 822-824 (1993).
Livingston et al., "Affinity chromatography of avian type C viral reverse transcriptase: Studies with Rous Sarcoma Virus transformed rat cells," *Virology*, 50:388-395 (1972).
Mattila et al., "Fidelity of DNA synthesis by the *Thermococcus litoralis* DNA polymerase—an extremely heat stable enzyme with proofreading activity," *Nucleic Acids Research*, 19(18):4967-4973 (1991).
Morrison et al., "Eukaryotic DNA polymerase amino acid sequence required for 3'→5' exonuclease activity," *Proc. Natl. Acad. Sci. USA*, 88:9473-9477 (1991).
Perrino et al., "Differential extension of 3' mispairs is a major contribution to the high fidelity of calf thymus DNA polymerase-α," *J. Biol. Chem.*, 264:2898-2905 (1989).
Sears et al., "CircumVent™ thermal cycle sequencing and alternative manual and automated DNA sequencing protocols using the highly thermostable $Vent_R$™ (exo-) DNA polymerase," *BioTechniques*, 13(4):626-633 (1992).

Uemori et al., "Organization and nucleotide sequence of the DNA polymerase gene from the archaeon *Pyrococcus furiosis*," *Nucleic Acids Research*, 21(2):259-265 (1993).
The Stratagene Catalog, Gene Characterization Kits, p. 39 (1988).
Supplementary Preliminary Amendment filed Jul. 18, 2003.
Office Action mailed Feb. 14, 2006.
Response including Declaration of Joseph A. Sorge and Rebecca L. Mullinax Under 37 C.F.R. § 1.131, filed Jul. 14, 2006.
Office Action mailed Aug. 16, 2006.
Preliminary Amendment filed Sep. 19, 2005, in U.S. Appl. No. 11/230,945.
Request for Additional Decision, filed by Morrison and Foerster on Jun. 10, 2003.
Letter Submitting Copy of Request by Takara Bio Inc. for Leave to Participate in this Reexamination as a Partial Assignee (Co-owner) and other Takara Bio Inc. Submissions filed Aug. 18, 2003.
Information Disclosure Statement by Takara Bio Inc. as a Partial Assignee (Co-Owner) and Form PTO 1449, filed by Fish and Richardson P.C. on Jan. 22, 2004.
Decision Returning Petition mailed Jan. 30, 2004.
Decision Returning Petition received Feb. 5, 2004.
Decision Returning Improper Paper mailed Feb. 6, 2004.
Office Action in Ex Parte Reexamination mailed Mar. 10, 2004.
Amendment filed May 10, 2004.
Decision Merging Reexamination Proceedings mailed Aug. 19, 2004.
Office Action in Ex Parte Reexamination mailed Dec. 20, 2004.
Response, including copy of Declaration of Jospeh A.. Sorge and Rebecca L. Mullinax Under 37 C.F.R. § 1.131 with Exhibits A & B; copy of Amendment Under 37 C.F.R. § 1.115, and copy of Eli Lilly v. Board of Regents of the University of Washington, filed Feb. 22, 2005.
Office Action in Ex Parte Reexamination mailed Mar. 28, 2005.
Response with copy of Louis v. Okada, filed May 31, 2005.
Declaration of Joseph A. Sorge Under 37 C.F.R. § 41.202(d), with Exhibits 1-69, filed May 31, 2005.
Declaration of Rebecca Mullinax, without Exhibits 1-69, filed May 31, 2005.
Declaration of Ronni L. Sherman, without Exhibits 1-69, filed May 31, 2005.
Declaration of Denise Wyborski, without Exhibits 1-9, filed May 31, 2005.
Declaration of Erikka Breedlove filed May 31, 2005.
Notice of Intent to Issue Ex Parte Reexamination Certificate mailed Sep. 26, 2005.
Petition Under 37 C.F.R. § 1.181(a)(3) to the Director in Person Requesting Withdrawal of Improper Notice of Intent to Issue Reexamination Certificate submitted by Takara Bio, with Exhibits A-H, filed by Morrison and Foerster on Oct. 18, 2005.
Decision Dismissing and Returning Petition mailed Dec. 22, 2005.
Renewed Petition Under 37 C.F.R. § 1.181 Requesting Withdrawal of Improper Notice of Intent to Issue Reexamination Certificate submitted by Takara Bio, with Exhibits A-H, filed by Morrison and Foerster on Jan. 4, 2006.
Decision Dismissing and Returning Petition mailed Jan. 30, 2006.
Letter to John M. Whealan, Esq., Deputy General Counsel for Intellectual Property Law and Solicitor at the U.S. Patent and Trademark Office, dated Feb. 8, 2006, with Exhibits A to D.
Office Action in Ex Parte Reexamination mailed Mar. 23, 2006.
Response, including copies of Pall Corp. v. Micron Separations, Inc. and Declaration of Wayne M. Barnes dated May 27, 1994, filed May 23, 2006.
Notice of Intent to Issue Ex Parte Reexamination Certificate mailed Jul. 20, 2006.
Comments on Statement of Reasons for Patentability and/or Confirmation filed Aug. 16, 2006.
Petition Under 37 CFR. §§ 1.181 and 1.183 Requesting Withdrawal of Improper Notice of Intent to Issue Reexamination Certificate, with Exhibits A to I, filed by Morrison and Foerster on Sep. 8, 2006.
Letter to John M. Whealan, Esq., Deputy General Counsel for Intellectual Property Law and Solicitor at the U.S. Patent and Trademark Office, dated Sep. 14, 2006, with Exhibits A to I.

Request for Reexamination Under 37 C.F.R. § 1.510 with Exhibits A-K, filed by Morrison and Foerster on Apr. 9, 2004.
Notice of Reexamination Request Filing Date mailed Apr. 28, 2004.
Notice of Assignment of Reexamination Request mailed Apr. 28, 2004.
Order Granting/Denying Request for Ex Parte Reexamination mailed May 28, 2004.
Amendment filed Sep. 2, 2004.
Declaration-Bd.R. 203(d) mailed Oct. 12, 2005.
Sorge Clean Copy of Claims filed Oct. 26, 2005.
Barnes's Clean Copy of Claims filed Oct. 26, 2005.
Seventh Stipulated Extension of Time filed May 24, 2006.
Barnes's Request for Entry of Adverse Judgment mailed Jun. 12, 2006.
Judgment—Request for Adverse—Bd.R. 127(b) filed Jun. 22, 2006.
Errata filed Jun. 29, 2006.
Jones, C.H. et al., "DNA Mutagenesis and Recombination," *Nature* 344(6268):793-794 (1990).
Kunkel, Thomas A., "Rapid and Efficient Site-Specific Mutagenesis Without Phenotypic Selection," *Proceedings of the National Academy of Sciences, USA* 82:488-492 (1985).
Landt, Olfert et al., "A General Method for Rapid Site-Directed Mutagenesis Using the Polymerase Chain Reaction," *Gene* 96:125-128 (1990).
Nassal, Michael and Rieger, Andrea, "PCR-Based Site-Directed Mutagenesis Using Primers with Mismatched 3'-ends."
Nelson, Richard M. and Long, George L., "A General Method of Site-Specific Mutagenesis Using a Modification of the *Thermus aquaticus* Polymerase Chain Reaction," *Analytical Biochemistry* 180:147-151 (1989).
Taylor, John W. et al., "The Rapid Generation of Oligonucleotide-Directed Mutations as High Frequency Using Phosphorothioate-Modified DNA," *Nucleic Acids Research* 13(24):8765-8775 (1985).
Vallete, Francois et al., "Construction of Mutant and Chimeric Genes Using the Polymerase Chain Reaction," *Nucleic Acids Research* 17(2):723-733 (1989).
Vandeyar, Mark A. et al., "A Simple and Rapid Method for the Selection of Oligodeoxynucleitide-Directed Mutants," *Genes* 65:129-133 (1989).
Watkins, Brynmor A. et al., "A Rapid Method for Site-Specific Mutagenesis Using Larger Plasmids as Templates," *BioTechniques* 15(4):700-704 (1993).
Weiner, Michael P. et al., "A Method for the Site-Directed Mono- and Multi-Mutagenesis of Double-Stranded DNA," *Gene* 126:35-41 (1993).
Yao, Zhengbin et al., "Site-Directed Mutagenesis of Herpesvirus Glycoprotein Phosphorylation Sites by Recombination Polymerase Chain Reaction," *PCR Methods and Applications* 1(3):205-207 (1992).
Ohler et al., PCR Methods and Applications 2:51-59 (1992).
Zhu, Yu Sheng et al., "The Use of Exonuclease III for Polymerase Chain Reaction Sterilization," *Nucleic Acids Research* 19(9):2511 (1991).
Clark, J.M. et al., "Novel Blunt-End Addition Reactions Catalyzed by DNA Polymerase 1 of *Escherichia coli*," *Journal of Molecular Biology* 198:123-127 (1987).
Clark, James M., "Novel Non-Templated Nucleotide Addition Reactions Catalyzed by Procaryotic and Eucaryotic DNA Polymerase," *Nucleic Acids Research* 16:9677-9686 (1988).
Deng, Win Ping and Nickoloff, Jac A. "Site-Directed Mutagenesis of Virtually any Plasmid by Eliminating a Unique Site," *Analytical Biochemistry* 200:81-88 (1992).
Hall, Len and Emery, David C. "A Rapid and Efficient Method for Site-Directed Mutagenesis by PCR, Using Biotinylated Universal Primers and Streptavidin-Coated Magnetic Bead," *Protein Engineering* 4(5):601.
Hemsley, Anne et al., "A Simple Method for Site-Directed Mutagenesis Using the Polymerase Using the Polymerase Chain Reaction," *Nucleic Acids Research* 17(16):6545-6551 (1989).
Ho, Steffan N. et al., "Site-Directed Mutagenesis by Overlap Extension Using the Polymerase Chain Reaction," *Gene* 77(1):51-59 (1989).

Hu, Gengxi, "DNA Polymerase-Catalyzed Addition of Nontemplated Extra Nucleotides to the 3'End of a DNA Fragement," *DNA and Cell Biology* 12:(8):763-770 (1993).

Hultman, Thomas et al., "Solid Phase in vitro Mutagenesis Using Plasmid DNA template," Nucleic Acids Research 18(17):5107-5111 (1990).

Jones, Douglas H. and Winistorfer, Stanley C., "Recombinant Circle PCR and Recombination PCR for Site-SpecificMutagenesis Without PCR Product Purification," *BioTechniques* 12(4):528-533 (1992).

Garrity et al., "Effects of different DNA polymerases in ligation-mediated PCR: Enhanced genomic sequencing and in vivo footprinting," *Proc. Natl. Acad. Sci. USA*, 89:1021-1025 (1992).

Livak et al., "Detection of single base differences using biotinylated nucleotides with very long linker arms," *Nucl. Acids Res.*, 20(18):4831-4837 (1992).

Whitcomb et al., "A new PCR based method for the generation of nested deletions," *Nucl. Acids Res.*, 21(17):4143-4146 (1993).

Letter from Morrison & Foerster dated Mar. 21, 2007.

Office Action mailed Mar. 12, 2007, in U.S. Appl. No. 11/230,945, filed Sep. 19, 2005.

Applicant Statement of Interview Summary filed Aug. 14, 2006, in U.S. Appl. No. 10/319,778.

Notice of Allowance and Fee(s) Due mailed Nov. 20, 2006, in U.S. Appl. No. 10/319,778.

Comments on Statement of Reasons for Allowance filed Nov. 27, 2006, in U.S. Appl. No. 10/319,778.

Notice of Allowance and Fee(s) Due mailed Mar. 8, 2007, in U.S. Appl. No. 10/319,778.

Office Action mailed Jan. 25, 1995, in U.S. Appl. No. 08/164,290.

Response to Restriction Requirement Under 35 U.S.C. § 121 dated Feb. 24, 1995, in U.S. Appl. No. 08/164,290.

Office Action mailed May 1, 1995, in U.S. Appl. No. 08/164,290.

Examiner Interview Summary Record mailed Jun. 14, 1995, in U.S. Appl. No. 08/164,290.

Response to Office Action dated Jul. 14, 1995, in U.S. Appl. No. 08/164,290.

Official Communication mailed Mar. 19, 1996, in U.S. Appl. No. 08/164,290.

Office Action mailed Aug. 5, 1996, in U.S. Appl. No. 08/164,290.

Request for Reconsideration Under 37 C.F.R. § 1.111 dated Dec. 5, 1996, in U.S. Appl. No. 08/164,290.

Office Action mailed Mar. 18, 1997, in U.S. Appl. No. 08/164,290.

Response to Office Action dated Sep. 17, 1997, in U.S. Appl. No. 08/164,290.

Express Abandonment dated Dec. 5, 1997, in U.S. Appl. No. 08/164,290.

Notice of Abandonment mailed Dec. 8, 1997, in U.S. Appl. No. 08/164,290.

Petition to Reopen Prosecution for Consideration of Additional Documents dated Jan. 30, 2007, in Reexamination Control No. 90/006,571.

Interview dated Feb. 5, 2007, in Reexamination Control No. 90/006,571.

*Ex Parte* Reexamination Communication Transmittal Form and Decision on Petition Under 37 C.F.R. § 1.182, mailed Mar. 28, 2007, in Reexamination Control No. 90/006,571.

*Ex Parte* Reexamination Interview Summary dated Jun. 27, 2007, in Reexamination Control No. 90/006,571.

*Ex Parte* Reexamination Communication Transmittal Form mailed Jun. 27, 2007, in Reexamination Control No. 90/006,571.

Interview Summary (and Certificate of Service) with attached slides and Decision on Appeal from U.S. Appl. No. 08/453,347 dated Jul. 20, 2007, in Reexamination Control No. 90/006,571.

\* cited by examiner

SEQUENCE LISTING (1) GENERAL INFORMATION:

(iii) NUMBER OF SEQUENCES: 44

(2) INFORMATION FOR SEQ ID NO: 1:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 1:

GTCCTGTCCG AGGTGCAGCT GCTCGAGTCT GG                      32

(2) INFORMATION FOR SEQ ID NO: 2:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 2:

AGGTGCAGCT GCTCGAGTCT GG                                  22

(2) INFORMATION FOR SEQ ID NO: 3:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 3:

AGGTGCAGCT GCTCGAGTCT GT                                  22

(2) INFORMATION FOR SEQ ID NO: 4:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 4:

AGGTGCAGCT GCTCGAGTCT TT                                        22

(2) INFORMATION FOR SEQ ID NO: 5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 5:

AGGTGCAGCT GCTCGAGTCT GGT                                       23

(2) INFORMATION FOR SEQ ID NO: 6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 6:

AGGTGCAGCT GCTCGAGTCT GTT                                       23

(2) INFORMATION FOR SEQ ID NO: 7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 7:

AGCATCACTA GTACAAGATT TGGGCTC                                   27

(2) INFORMATION FOR SEQ ID NO: 8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 8:

CGGGAGATCA TGAGGGTGTC CTT                                       23

(2) INFORMATION FOR SEQ ID NO: 9:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 9:

ATATACTAGT GAGACAGTGA CCAGGGTTCC TTGGCCCCA                   39

(2) INFORMATION FOR SEQ ID NO: 10:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 10:

GTGCCAGATG TGAGCTCGTG ATGACCCAGT CTCCA                       35

(2) INFORMATION FOR SEQ ID NO: 11:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 11:

TCCTTCTAGA TTACTAACAC TCTCCCCTGT TGAAGCTCTT TGTGACGGGC GAACTC      56

(2) INFORMATION FOR SEQ ID NO: 12:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 12:

GTCTCACTAG TCTCCACCAA GGGCCCATCG GTC                         33

(2) INFORMATION FOR SEQ ID NO: 13:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 13:

CGGGAGATCA TGAGGGTGTC CTT                         23

(2) INFORMATION FOR SEQ ID NO: 14:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 14:

CTCAGTATGG TGGTTGTGC                              19

(2) INFORMATION FOR SEQ ID NO: 15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 15:

CCGGAATTCT TATCATTTAC CCGGAGA                     27

(2) INFORMATION FOR SEQ ID NO: 16:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 16:

ATTAACCCTC ACTAAAG                                17

(2) INFORMATION FOR SEQ ID NO: 17:

(i) SEQUENCE CHARACTERISTICS:
        (A) LENGTH: 17 base pairs

```
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 17:

AATACGACTC ACTATAG                                                       17

(2) INFORMATION FOR SEQ ID NO: 18:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 18:

TCCTTCTAGA TTACTAACAC TCTCCCCTGT TGAA                                    34

(2) INFORMATION FOR SEQ ID NO: 19:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 19:

CTGCACAGGG TCCTGGGCCG AGCTCGTGGT GACTCAG                                 37

(2) INFORMATION FOR SEQ ID NO: 20:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 20:

GCATTCTAGA CTATTAACAT TCTGTAGGGG C                                       31

(2) INFORMATION FOR SEQ ID NO: 21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear
```

(ii) MOLECULE TYPE: DNA (genomic)

(iii) HYPOTHETICAL: NO (iv) ANTI-SENSE: NO (xi) SEQUENCE DESCRIPTION: SEQ ID NO: 21:

AGGTCCAGCT GCTCGAGTCT GG                                                   22

(2) INFORMATION FOR SEQ ID NO: 22:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 22:

AGGCTTACTA GTACAATCCC TGGGCACAAT                                            30

(2) INFORMATION FOR SEQ ID NO: 23:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 23:

CCGTTACTAG TAGCCAAAAC GACACCCCCA TCTGTC                                     36

(2) INFORMATION FOR SEQ ID NO: 24:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 24:

CCTGAGGGCT CCCAGAGAGT GG                                                   22

(2) INFORMATION FOR SEQ ID NO: 25:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 25:

GGTTTAGCAC GACCACAACA GC                                                22

(2) INFORMATION FOR SEQ ID NO: 26:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 26:

AATACGACTC ACTATAG                                                      17

(2) INFORMATION FOR SEQ ID NO: 27:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 27:

AATACGACTC ACTATAG                                                      17

(2) INFORMATION FOR SEQ ID NO: 28:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 28:

GGCTGGTGTC ACCTGTGTTA                                                   20

(2) INFORMATION FOR SEQ ID NO: 29:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 29:

CCTTAGGAGG AACAAGTCCC                                                        20

(2) INFORMATION FOR SEQ ID NO: 30:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 30:

CTTGAAGATC TATGCTTAAA CAGGTAG                                                27

(2) INFORMATION FOR SEQ ID NO: 31:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 31:

CATGTGAATT CTTAAACTTC AACTTGG                                                27

(2) INFORMATION FOR SEQ ID NO: 32:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 32:

GGTGGCGACG ACTCCTGGAG CCC                                                    23

(2) INFORMATION FOR SEQ ID NO: 33:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 33:

GACAGTCACT CCGGCCCGTG CGG                                                    23

(2) INFORMATION FOR SEQ ID NO: 34:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 34:

AAGCTTCAGG AAAACAGTGA GCAGCGCCTC                                              30

(2) INFORMATION FOR SEQ ID NO: 35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 35:

AGTCAGGTAT CTTTGACAGT                                                         20

(2) INFORMATION FOR SEQ ID NO: 36:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 36:

GGAATTCGTA ACAGCACTTA CGGTAGC                                                 27

(2) INFORMATION FOR SEQ ID NO: 37:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 37:

AGCACTCATA AGTGACACCC                                                         20

(2) INFORMATION FOR SEQ ID NO: 38:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 38:

CATAGCGAAT TCGCAAAACC TTTCGCGGTA TGG                33

(2) INFORMATION FOR SEQ ID NO: 39:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 39:

ACTACGGAAT TCCACGGAAA ATGCCGCTCA TCC                33

(2) INFORMATION FOR SEQ ID NO: 40:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 40:

AGGTGCAGCT GCTCGAGTCG GG                           22

(2) INFORMATION FOR SEQ ID NO: 41:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 41:

AGGTGCAACT GCTCGAGTCT GG                           22

(2) INFORMATION FOR SEQ ID NO: 42:

(i) SEQUENCE CHARACTERISTICS:

```
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 42:

AGGTGCAACT GCTCGAGTCG GG                                    22

(2) INFORMATION FOR SEQ ID NO: 43:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 43:

TTGACTCGAG TAATCTGAGC TAAAGTCTAG AGCGCTGAGG GTGACGATCC      50

(2) INFORMATION FOR SEQ ID NO: 44:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 44:

ATGGCAACTA GTTATCAGCT TGCTTTCGAG G                          31
```

POLYMERASE COMPOSITIONS AND USES THEREOF

RELATED APPLICATIONS

This is a continuation of application Ser. No. 08/197,791 filed Feb. 16, 1994 now U.S. Pat. No. 5,556,772 which is a CIP of application Ser. No. 08/164,290 filed Dec. 8, 1993 now abandoned.

FIELD OF THE INVENTION

The present invention is related to the field of molecular biology, and more particularly, to polynucleotide synthesis.

BACKGROUND OF THE INVENTION

DNA polymerases catalyze the synthesis of DNA and can be found in all cells as well as being encoded in numerous viruses. Although all DNA polymerases possess 5'–3' DNA polymerase activity, DNA polymerases differ from one another in numerous other properties. For example, some enzymatic activities that are possessed by some DNA polymerases, but absent in other DNA polymerases include: double stranded DNA 5'–3' exonuclease activity, single-stranded DNA 3'–5' exonuclease activity, double-stranded 3'–5' DNA exonuclease activity, RNase H activity, reverse transcriptase activity, and the like. Additionally, different DNA polymerases may have different optimal pH and temperature ranges for activity. Furthermore, DNA polymerases may differ in the rate in which they catalyze DNA synthesis.

Purified DNA polymerases have numerous uses in vitro. A detailed description of DNA polymerases, including methods for their isolation, can be found among other places, in *DNA Replication* 2nd edition, by Kornberg and Baker, W.H. Freeman & Company, New York, N.Y. 1991. In vitro uses of DNA polymerases include, for example, the labeling and synthesis of hybridization probes, DNA sequencing, and DNA amplification. A DNA amplification method employing DNA polymerases that has been particularly useful is the polymerase chain reaction (PCR) technique. The technique of PCR is described in numerous publications, including, *PCR: A Practical Approach*, M. J. McPherson, et al., IRL Press (1991), PCR Protocols: *A Guide to Methods and Applications*, by Innis, et al., Academic Press (1990), and *PCR Technology: Principals and Applications for DNA Amplification*, H. A. Erlich, Stockton Press (1989). PCR is also described in many U.S. patents, including U.S. Pat. Nos. 4,683,195; 4,683,202; 4,800,159; 4,965,188; 4,889,818; 5,075,216; 5,079,352; 5,104,792; 5,023,171; 5,091,310; and 5,066,584, which are hereby incorporated by reference. The PCR technique typically involves the step of denaturing a polynucleotide, followed by the step of annealing at least a pair of primer oligonucleotides to the denatured polynucleotide, i.e., hybridizing the primer to the denatured polynucleotide template. After the annealing step, an enzyme with polymerase activity catalyzes synthesis of a new polynucleotide strand that incorporates the primer oligonucleotide and uses the original denatured polynucleotide as a synthesis template.

In many instances, a given DNA polymerase may fail to synthesize the desired polynucleotide product. These failures may be attributable to a number of reasons including such problems as template and primer base pair mismatches, lack of proofreading, insufficient rate of synthesis, high misincorporation rate, inability to transcribe GC or AT rich regions, lack of sufficient processivity (processivity refers to the length of synthesis product formed before the polymerase stops synthesis), etc. It is therefore of interest to provide new methods and compositions for improved polynucleotide synthesis over a wide variety of experimental conditions.

SUMMARY OF THE INVENTION

The subject invention provides novel compositions containing a mixture of (a) an enzyme that possesses substantial 3'–5' exonuclease activity and (b) a DNA polymerase with less 3'–5' exonuclease activity than the enzyme possessing substantial 3'–5' exonuclease activity. Preferably, the enzyme with substantial 3'–5' exonuclease activity is a DNA polymerase. Preferably, the DNA polymerase with less 3'–5' exonuclease activity than the enzyme possessing substantial 3'–5' exonuclease activity is a DNA polymerase substantially lacking 3'–5' exonuclease activity. When a step in a technique of interest employing polynucleotide synthesis involves the step of incubation at an elevated temperature, e.g., PCR, both the DNA polymerase and the enzyme with substantial 3'–5' exonuclease activity are thermostable enzymes. A preferred embodiment of the invention is a composition comprising the Taq DNA polymerase (from *Thermus aquaticus*) and the Pfu DNA polymerase (from *Pyrococcus furiosus*).

Another aspect of the invention is to provide methods for synthesizing polynucleotides, typically DNA, using compositions comprising an enzyme that possesses substantial 3'–5' exonuclease activity and DNA polymerase with less 3'–5' exonuclease activity than the enzyme with substantial 3'–5' exonuclease activity. Preferably, the DNA polymerase used in the provided methods is a DNA polymerase that substantially lacks 3'–5' exonuclease activity. The methods of synthesizing DNA (or other polynucleotides) provided comprise the step of mixing a composition containing (a) an enzyme possessing substantial 3'–5' exonuclease activity and (b) a DNA polymerase with less 3'–5' exonuclease activity than the enzyme with substantial 3'–5' exonuclease activity. Other reagents required for polynucleotide synthesis include nucleotide triphosphates (dNTPs), polynucleotide primers, a synthesis template, and the like.

Another aspect of the invention is to use the subject method of polynucleotide synthesis to carry out the synthesis step in a polymerase chain reaction experiment.

Yet another aspect of the invention is to provide kits for the synthesis of polynucleotides, wherein the kits comprise an enzyme that possesses substantial 3'–5' exonuclease activity and a DNA polymerase with less 3'–5' exonuclease activity than the enzyme with substantial 3'–5' exonuclease activity, preferably a DNA polymerase substantially lacking 3'–5' exonuclease activity. Preferably, the enzyme with substantial 3'–5' exonuclease activity is a DNA polymerase. The kits may also contain polynucleotide precursors, synthesis primers, synthesis templates, buffers, and the like.

DESCRIPTION OF SPECIFIC EMBODIMENTS

The subject invention provides novel composition for use in synthesizing polynucleotides, particularly DNA. The subject compositions comprise an enzyme that possesses substantial 3'–5' exonuclease activity and a DNA polymerase with less 3'–5' exonuclease activity than the enzyme with substantial 3'–5' exonuclease activity. In a preferred embodiment of the invention, the DNA polymerase in the compositions is a DNA polymerase that substantially lacks 3'–5' exonuclease activity. The enzyme that possesses substantial 3'–5' exonuclease activity is preferably a DNA polymerase. Prior to the inventors' work, DNA synthesis in vitro was performed with a single purified DNA polymerase. In a variety of synthesis procedures, the subject compositions provide superior synthesis results, as compared with the synthesis results obtained with a single DNA polymerase with less 3'–5' exonuclease activity than the enzyme with 3'–5' exonuclease activity alone (including synthesis results obtained with DNA polymerases that substantially lack 3'–5' exonuclease activity).

Although compositions comprising a DNA polymerase with less 3'–5' exonuclease activity than the enzyme possessing substantial 3'–5' exonuclease activity may produce superior results in a variety of synthesis experiments, the composition is especially useful in DNA synthesis when there exists one or more mismatched nucleotide(s), particularly mismatches at the 3' end of one or more synthesis primer(s). In such situations, the results achieved, i.e., the amount of synthesis product produced, are significantly greater than the amount of synthesis product obtained using either a DNA polymerase with less 3'–5' exonuclease activity than the enzyme possessing substantial 3'–5' exonuclease activity or with a DNA polymerase possessing substantial 3'–5' exonuclease activity alone. Other advantages of the subject compositions and methods include increased synthesis product yield, increased transcription product length, and the synthesis of polynucleotides that can not be synthesized by a given DNA polymerase alone.

The enzyme possessing substantial 3'–5' exonuclease activity for use in the subject compositions and methods may be any enzyme possessing substantial 3'–5' single-stranded DNA exonuclease activity. Enzymes possessing substantial 3'–5' exonuclease activity for use in the present compositions and methods may be isolated from natural sources or produced through recombinant DNA techniques. Enzymes that possess substantial 3'–5' exonuclease activity and their properties are described in detail in, among other places, *DNA Replication* 2nd edition, Kornberg and Baker, supra and *Enzymes*, supra. Examples of enzymes that possess substantial 3'–5' exonuclease activity include *E. coli* exonuclease I, *E. coli* exonuclease III, *E. coli* recBCD nuclease, mung bean nuclease, and the like. Preferred enzymes with substantial 3'–5' exonuclease activity for use in the subject compositions and methods are DNA polymerases that possess substantial 3'–5' exonuclease activity.

DNA polymerases that possess substantial 3'–5' exonuclease activity include the Pfu DNA polymerase, *E. coli* DNA polymerase I, Klenow fragment, T-4 polymerase, T-7 polymerase, *E. coli* DNA pol III, Ultima DNA Polymerase (Cetus), Vent DNA and Deep Vent DNA polymerases (New England Biolabs). When using the subject compositions in reaction mixtures that are exposed to elevated temperatures, e.g., during the PCR technique, use of thermostable DNA polymerases is preferred. Examples of the thermostable DNA polymerases that possess substantial 3'–5' exonuclease activity include Vent DNA polymerase, Ultima DNA polymerase, Deep Vent DNA polymerase, and Pfu DNA polymerases. A particularly preferred DNA polymerase possessing 3'–5' exonuclease activity for use in subject composition is the Pfu DNA polymerase. The Pfu DNA polymerase is commercially available from Stratagene (La Jolla, Calif.). A detailed description of the Pfu DNA polymerase can be found, among other places in U.S. patent application Ser. No. 07/803,627 filed Dec. 2, 1991.

DNA polymerases and their properties are described in detail in, among other places, *DNA Replication* 2nd edition, Kornberg and Baker, W.H. Freeman, New York, N.Y. (1991). DNA polymerases with less 3'–5' exonuclease activity for use in the subject compositions and methods may be isolated from natural sources or produced through recombinant DNA techniques. DNA polymerases with less 3'–5' exonuclease activity than the 3'–5' exonuclease activity of the enzyme with substantial 3'–5' exonuclease activity, i.e., 3'–5' single-stranded exonuclease activity, include Taq DNA polymerases and Sequenase™ (modified bacteriophage T7 DNA polymerase, available from U.S. Biochemical, Columbus, Ohio), and the like. Additionally, the person of average skill in the art having the benefit of this disclosure will recognize that exonuclease deficient polymerases such as Exo⁻ Pfu DNA polymerase, Vent® (exo⁻) DNA polymerase, Deep Vent® (exo–) DNA polymerase, and the like may be suitably used in the subject compositions. Taq DNA polymerase, Sequenase™, Exo⁻ Pfu DNA polymerase, Vent (exo⁻) DNA polymerase, and Deep Vent (exo⁻) DNA polymerase are all examples of DNA polymerases that substantially lack 3'–5' exonuclease activity.

When using the subject compositions in reaction mixtures that are exposed to elevated temperatures, e.g., during the PCR technique, use of thermostable DNA polymerases is preferred. The subject composition may also be used with DNA polymerases that have not yet been isolated, provided that the DNA polymerases have less 3'–5' single-stranded DNA exonuclease activity than the enzyme with substantial 3'–5' exonuclease activity in the subject composition. Assays for both DNA polymerase activity and 3'–5' exonuclease activity can be found in *DNA Replication* 2nd Ed., Kornberg and Baker, supra, *Enzymes*, Dixon and Webb, Academic Press, San Diego, Calif. (1979), as well as other publications available to the person of ordinary skill in the art. A preferred DNA polymerase for use in the subject compositions and methods of the invention is the Taq DNA polymerase.

The term "substantially lacking 3'–5' exonuclease activity" when used in reference to a DNA polymerase, refers to those DNA polymerases that have less 3'–5' exonuclease activity than the enzyme included in the subject composition that has substantial 3'–5' exonuclease activity.

The term "thermostable" when used with respect to an enzyme, is readily understood by a person of ordinary skill in the art. Typically, a "thermostable" enzyme retains at least 50 percent of its specific activity after exposure to a temperature of 80° C. for a period of 20 minutes.

The ratio of the DNA polymerase with less 3'–5' exonuclease activity than the enzyme possessing substantial 3'–5' exonuclease activity to the enzyme possessing substantial 3'–5' exonuclease activity in the subject composition may be varied with respect to one another. The ratio of the DNA polymerase activity to 3'–5' exonuclease activity present in the subject composition employed in a given synthesis procedure may be readily optimized by performing a series of simple experiments in which the ratio of the DNA polymerase with less 3'–5' exonuclease activity than the enzyme with substantial 3'–5' exonuclease activity to the enzyme possessing substantial 3'–5' exonuclease activity are systematically varied with respect to one another and the synthesis results compared.

The subject compositions may be used in various methods of synthesizing polynucleotides in essentially the same manner as the DNA polymerase present in the subject composition. Typically, synthesis of a polynucleotide requires a synthesis primer, a synthesis template, polynucleotide precursors for incorporation into the newly synthesized polynucleotide, (e.g. dATP, dCTP, dGTP, dTTP), and the like. Detailed methods for carrying out polynucleotide synthesis are well known to the person of ordinary skill in the art and can be found, for example, in *Molecular Cloning* second edition, Sambrook et al., Cold Spring Harbor Laboratory Press, Cold Spring Harbor, N.Y. (1989). The process of PCR employs a polynucleotide synthesis step in each cycle; this polynucleotide synthesis step may be achieved using the subject compositions.

The invention herein also contemplates a kit format which comprises a package unit having one or more containers of the subject composition and in some embodiments including containers of various reagents used for polynucleotide synthesis, including synthesis in PCR. The kit may also contain one or more of the following items: polymerization enzymes, polynucleotide precursors, primers, buffers, instructions, and controls. Kits may include containers of reagents mixed together in suitable proportions for performing the methods in accordance with the invention. Reagent containers preferably contain reagents in unit quantities that obviate measuring steps when performing the subject methods.

The following examples are offered for the purpose of illustrating, not limiting, the subject invention.

BACKGROUND OF EXAMPLES

Characteristics of Taq and Pfu DNA Polymerases

*Thermus aquaticus* DNA Polymerase

*Thermus aquaticus* (Taq) DNA polymerase is a 94-kDa protein which does not have an inherent 3' to 5' exonuclease activity (Tindall, K. R., and T. A. Kunkel. 1988. Fidelity of DNA synthesis by the *Thermus aquaticus* DNA polymerase. *Biochemistry* 27:6008–6013). 3' to 5' exonuclease activity enables a polymerase to proofread and is therefore associated with fidelity of an enzyme. The estimated error rate of Taq varies from $2 \times 10^{-4}$ mutations per nucleotide per cycle during PCR (Saiki, R. K., D. H. Gelfand, S. Stoffel, S. J. Scharf, R. Higuchi, G. T. Horn, K. B. Mullis, and H. A. Erlich. Primer-directed enzymatic amplification of DNA with a thermostable DNA polymerase. 1988. *Science* 239: 487–491) to $2 \times 10^{-5}$ for nucleotide substitution errors in a single round of DNA synthesis of the lacZα gene (Eckert, K. A. and T. A. Kunkel. High fidelity DNA synthesis by the *Thermus aquaticus* DNA polymerase. 1990. *Nucleic Acids Res.* 18:3739–3744). The error rate of Taq DNA polymerase is important in polymerization because it reflects the ability of the polymerase to extend from a mismatched primer: template. Taq DNA polymerase has been shown to extend significantly less efficiently from a mismatched primer: template than from a correctly based paired primer:template (Innis, M. A., K. B. Myambo, D. H. Gelfand and M. A. D. Brow. DNA sequencing with *Thermus aquaticus* DNA polymerase and direct sequencing of polymerase chain reaction-amplification of DNA. 1988. *Proc. Natl. Acad. Sci. USA.* 85:9436–9440 and Kwok, S., D. E. Kellogg, D. Spasic, L. Goda, C. Levenson, and J. J. Sninsky. Effects of primer-template mismatches on the polymerase chain reaction: Human immunodeficiency virus type 1 model studies. 1990. *Nucleic Acids Res.* 18:999–1005).

Taq DNA polymerase is highly processive at an extension rate of >60 nucleotides per second at 70° C. on M13 phage DNA when using a GC-rich 30 mer as a primer (Innis, et al. 1988). The Taq genome is 66.8% GC (Munster, M. J., A. P. Munster, J. R. Woodrow, and R. J. Sharp. Isolation and preliminary taxonomic studies of *Thermus* strains isolated from Yellowstone National Park, USA. 1986. *J. of Gen. Microbiol.* 132:1677–1683).

*Pyrococcus furiosus* DNA Polymerase

*Pyrococcus furiosus* (Pfu) DNA polymerase is a 91-kDa protein which has an inherent 3' to 5' exonuclease activity. This proofreading activity allows Pfu to extend from mismatched primer:templates by first removing the mismatched base(s) followed by polymerization and results in an error rate of $1.6 \times 10^{-6}$ mutations per nucleotide per cycle in PCR reactions. The error rate of Pfu DNA polymerase is thus tenfold lower than that of Taq DNA polymerase and results in higher fidelity (Lundberg, K. S., D. D. Shoemaker, M. W. W. Adams, J. M. Short, J. A. Sorge, and E. J. Mathur. High-fidelity amplification using a thermostable DNA polymerase isolated from *Pyrococcus furiosus*. 1991. *Gene* 108: 1–6). The processivity of Pfu DNA polymerase is 10–15 nucleotides per second and its genome is 38% GC.

Templates cDNA Templates cDNAs from 2 sources, hybridoma and PBLs (peripheral blood lymphocytes), were chosen as templates in these experiments. Hybridoma cDNA from human anti-tetanus toxoid 9F12 (ATCC, HM-8177) and mouse anti-human fibronectin CG7C7 (ATCC, HB-126) express only one immunoglobulin heavy and light chain and therefore would contain a homogeneous population of heavy and light chain cDNAs. The 9F12 cDNA had amplified efficiently in previous experiments when using primers AB-61 or MK-205 with AB-76 (Fd) or MK-39 (VH), AB-25 and AB-94 (light chain[LC]), and MK-94 and AB-76 (CH1). Based on nucleotide sequence, 9F12 is a human IgG1 from the VHIII family with a kappa light chain. The SA-13 cDNA had amplified efficiently in previous experiments when using primers AB-19 with AB-41 (Fd) and AB-25 and AB-26 (LC). PBL cDNA expresses immunoglobulin heavy and light chains from all of the human heavy and light chain families (Kabat, T. T. Wu, H. Bilofsky, M. Reid-Milner, and H. Perry, eds. Sequences of Proteins of Immunological Interest, 1987, U.S. Public Health Service, Washington, D.C.) and therefore would contain a heterogenous population of heavy and light chain cDNAs. This cDNA had not amplified efficiently with primer AB-61 or MK-205 with AB-76 (Fd) or MK-39 (VH) but had amplified efficiency with AB-25 and AB-94 (LC) and MK-94 and AB-76 (CH1) (Table 13).

DNA Templates

Nine different DNA templates were also used in these experiments. The genomic DNAs were isolated from human, Epstein Barr virus, *Escherichia coli*, and transgenic and nontransgenic mouse. Plasmid DNAs were pBluescript II and pBluescript containing the light chain and Fd of an anti-tetanus toxoid immunoglobulin (Mullinax R. L., E. A. Gross, J. R. Amberg, B. N. Hay, H. H. Hogrefe, M. M. Kubitz, A. Greener, M. Alting-Mees, D. Ardourel, J. M. Short, J. A. Sorge, and B. Shopes. 1990. Identification of human antibody fragment clones specific for tetanus toxoid in a bacteriophage lambda immunoexpression library. *Proc. Natl. Acad. Sci. USA* 87:8095–8099).

Primer Design

The ability of an oligonucleotide to act as a primer in DNA synthesis is dependent on several factors: the kinetics of association and dissociation of the primer:template duplexes under the annealing and extension conditions, the effects of mismatched bases and their location on duplex stability, and the efficiency with which the polymerase can recognize and extend from a mismatched duplex. In general, single base pair mismatches at or near the terminal 3' base of a primer are known to affect the ability of the polymerase to bind and extend from the primer:template and therefore should have a significant effect on the efficiency of the priming reaction.

In particular, Taq DNA polymerase requires that 3 to 5 bases at the 3' end of the primer base pair exactly in order for polymerization to occur. The effect of other mismatches on the efficiency of polymerization is dependent on the number of mismatches and where they occur in the primer. This presents a problem when the exact template sequence is not known such as when the nucleotide sequence of the template is derived from amino acid sequence due to the redundancy of the amino acid code and when designing primers for templates of families of genes which are heterogeneous.

Four oligonucleotide primers designed to specifically prime the first constant region of human heavy chain immunoglobulin genes (VH) were designed based on the available nucleotide and amino acid sequences with the problems above in mind (Mullinax, et al., 1990). Because experimental results indicated poor priming and/or amplification efficiency with PBL templates with Taq DNA polymerase, we wanted to investigate how this efficiency could be improved.

One of the human heavy chain first constant region primers, AB-61 (Table 15) was chosen for examination. AB-61 has a dGTP as the 3' base and would require a dCTP in the corresponding position in the template in order for efficient priming to occur when Taq DNA polymerase was used for primer extension due to its lack of 3' to 5' exonuclease activity (Kwok, et al. 1990, supra). However, Pfu DNA polymerase does have 3' to 5' exonuclease activity and would remove any mismatched base(s) from the 3' end of the primer and would therefore be able to extend (Lundberg, et al. 1991, supra). Therefore it was of interest to investigate the effect of using Pfu DNA polymerase alone and in combination with Taq DNA polymerase in primer extension reactions using cDNA from hybridoma cell lines (9F12 and CG7C7) and from human PBLs as the template under various experimental conditions.

Kwok, et al. (1990) demonstrated that primer extension efficiency when using Taq DNA polymerase is independent of the dNTP in the template when a dTTP is the 3' base in the primer. Therefore the effect of the addition of one or more dTTPs in various positions at the 3' end of the primer AB-61 (Table 13) was also investigated.

Buffer Comparisons

Buffer conditions have been shown to effect the processivity, activity and fidelity of polymerases. In particular, the processivity and/or activity of Taq DNA polymerase are known to be affected by KCl, $MgCl_2$, $(NH_4)_2SO_4$, and NaCl concentrations. The fidelity of Taq DNA polymerase is also affected by the concentration of $MgCl_2$ relative to the total concentration of dNTPs (Eckert, et al. 1990, supra) and dNTP and $MnCl2$ concentrations (Leung, D. W., E. Chen, and D. V. Goeddel. 1989). A method for random mutagenesis of a defined DNA segment using a modified polymerase chain reaction. *Technique*. 1:11–15).

Table 17 lists the buffer components and their concentrations for the 10× Taq DNA polymerase and Pfu V25, #1, and #3 buffers used in these experiments.

Different Ratios of Taq and Pfu DNA Polymerases

Taq DNA polymerase is unable to correct nucleotide misincorporations made during polymerization due to its lack of 3' to 5' exonuclease activity. In general, this would result in the inability of Taq to extend from a newly polymerized strand annealed to a template when an incorrect nucleotide has been inserted. Pfu DNA polymerase has an inherent 3' to 5' exonuclease activity and would be able to remove the incorrectly inserted nucleotide and then extend from the correctly base paired primer:template. The ratio of the two polymerases may be critical for optimal efficiency of this process. We therefore compared several ratios of Taq: Pfu DNA polymerases to determine the effect on DNA synthesis from 3' matched and mis-matched primers.

In addition, Pfu DNA polymerase has been shown to degrade unannealed primers by its 3' to 5' exonuclease activity. These degraded primers would not be available in subsequent rounds of DNA amplification and would therefore effect the efficiency of the PCR reaction. It may therefore be desirable to have a low concentration of Pfu DNA polymerase relative to Taq DNA polymerase to decrease this effect.

Example 1

Primer Extension with Taq or Pfu DNA Polymerase in Separate Reactions

These experiments demonstrate the relative ability of Taq or Pfu DNA polymerase to PCR amplify hybridoma and PBL templates under various conditions. Taq DNA polymerase resulted in either the presence of a PCR product or an increase in the amount of PCR product when compared to Pfu DNA polymerase when amplifying hybridoma and PBL templates. In addition, the dNTP and not the $MgCl_2$ concentration affected the amount of LC product generated.

Taq and Pfu DNA Polymerases with CG7C7 Hybridoma Template

Taq and Pfu DNA polymerases were compared for their ability to amplify the LC, CH1, and Fd regions of a mouse anti-human fibronectin antibody (CG7C7, ATCC HB-126). Total RNA was isolated from CG7C7 hybridoma cells using an RNA isolation kit (Stratagene). Five µg of total RNA was converted to cDNA in a first strand synthesis reaction using an oligo-dT primer for the light chain and AB-41 for the heavy chain (Table 15). mRNA was annealed to the first strand primer at 65° C. for 5 minutes followed by cooling at room temperature for 30 minutes. First strand reactions were performed in 1× first strand buffer [1× first strand buffer is 75 mM KCl; 50 mM tris-Cl, pH 8.3; 10 mM dithiothreitol; 3 mM $MgCl_2$; 1 Unit RNase Block II (Stratagene)], 375 µM each dNTP and 20 Units Moloney-Murine Leukemia Virus Reverse Transcriptase (M-ML VRT) (Stratagene)] and incubated at 37° C. for 1 hour and then 42° C. for 30 minutes.

PCR primers used to amplify the LC were AB-25 and AB-26, CH1 were MK-501 and AB-41, Fd were AB-41 and AB-19, and the polylinker region of pBluescript were T3 and T7 (Table 14). PCR reactions with Taq DNA polymerase were at a primer concentration of 0.2 µM of each 5' and 3' primer in 1× Taq buffer (Table 17) with 200 µM each dNTP and 2.5 units Taq DNA polymerase (Stratagene; La Jolla, Calif.) using 1/10 of cDNA prepared in the first strand reaction as the template. Samples were denatured at 99° C. for 5 minutes and annealed at 54° C. for 5 minutes followed by PCR amplification at 72° C. for 3 minutes, 93° C. for 1.5 minutes and 54° C. for 2 minutes for 30 cycles.

PCR reactions with Pfu DNA polymerase were performed under the same conditions but with 1× V25 buffer instead of Taq buffer.

Twenty µl of the 100 µl reaction was separated on an agarose gel by electrophoresis and visualized by staining with ethidium bromide. Results are indicated by the relative amount of appropriately sized PCR product and all given in Table 1.

TABLE 1

Taq and Pfu DNA polymerases with CG7C7 template

| Product | Primers | Taq buffer Taq | V25 buffer Pfu |
|---------|---------|----------------|----------------|
| Fd | AB-19/AB-41 | 2+ | +/− |
| CH1 | MK-501/AB-41 | 2+ | + |
| LC | AB-25/AB-26 | + | − |
| polylinker | T3/T7 | + | − |

*The relative amounts of PCR product are indicated as a range of no product (−) to the most product (5+).

Results from this experiment indicate that only Taq DNA polymerase produced an appropriately sized PCR product with all of the primer pairs used. Pfu DNA polymerase produced either less or no product when compared to Taq DNA polymerase with all of the primer pairs.

The CH1 primers were designed for amplification of constant regions of the antibody heavy chain and would be expected to base pair match perfectly with their template. The T3 and T7 primers also base pair match perfectly with the pBluescript template.

Taq and Pfu DNA Polymerases with PBL Template

Taq DNA polymerase was used to amplify the LC (both kappa and lambda), CH1, CH2/CH3, and Fd regions of human PBL immunoglobulins. The $MgCl_2$ and dNTP concentrations were varied to try to increase the amount of PCR product generated. Total RNA was isolated from human PBLs using an RNA isolation kit (Stratagene). Five ug of total RNA was converted to cDNA in a first strand synthesis reaction using an oligo-dT primer for the LC, and MK-25 for the heavy chain. mRNA was annealed to the first strand primer at 65° C. for 5 minutes followed by cooling at room temperature for 30 minutes. First strand reactions were performed in 1× first strand buffer [1× first strand buffer is 75 mM KCl; 50 mM tris-Cl, pH 8.3; 10 mM dithiothreitol; 3 mM $MgCl_2$; 1 Unit RNase Block II (Stratagene)], 375 µM each dNTP and 20 Units Moloney-Murine Leukemia Virus Reverse Transcriptase (M-MLVRT) (Stratagene)] and incubated at 42° C. for 1 hour.

PCR primers used to amplify the kappa LC were AB-25 and AB-26, lambda LC were AB-92 and AB-28, CH2/CH3 were MK-25 and MK-26, Fd were AB-52 with AB-61, AB-62, AB-63, or AB-64 (Table 18). PCR reactions were at a primer concentration of 0.2 µM of each 5' and 3' primer in 1× Taq buffer (Table 17) with 2.5 units Taq DNA polymerase using 1/10 of cDNA prepared in the first strand reaction as the template. The kappa LC reaction was 2.0 mM $MgCl_2$ with 237.5 µM dNTPs, the lambda LC reaction was 1.8 mM $MgCl_2$ at 137.5 µM or 237.5 µM dNTPs, the Fd reactions were 1.9 mM $MgCl_2$ with 187.5 µM dNTPs, and the CH2/CH3 reactions were at 1.5 mM $MgCl_2$ with 137.5 µM dNTPs. Samples were denatured at 94° C. for 5 minutes and annealed at 54° C. for 5 minutes followed by PCR amplification at 72° C. for 2.5 minutes, 93° C. for 1 minute and 54° C. for 1.5 minutes for 40 cycles. Samples were analyzed as described above. Results are indicated by the relative amount of appropriately sized PCR product and are given in Table 2.

TABLE 2

Taq and Pfu DNA polymerases with PBL template
PBL template

| | | 1.9 mM $MgCl_2$ 187.5 µM dNTP | 1.8 mM $MgCl_2$ | | 2.0 mM $MgCl_2$ | |
|---|---|---|---|---|---|---|
| primers | product | | 137.5 µM dNTP | 237.5 µM dNTP | 137.5 µM dNTP | 237.5 µM dNTP |
| AB-61/AB-52 | Fd | — | | | | |
| AB-62/AB-52 | Fd | — | | | | |
| AB-63/AB-52 | Fd | — | | | | |
| AB-64/AB-52 | Fd | — | | | | |
| MK-25/MK-26 | CH2/3 | — | — | — | — | — |
| AB-25/AB-26 | kappa LC | | | | | 4+ |
| AB-92/AB-28 | lambda LC | | + | 4+ | + | 4+ |

Only the kappa and lambda LC reactions produced a specific PCR product. The 1.8 and 2.0 mM $MgCl_2$ with 137.5 µM dNTP lambda LC reactions produced only a very small amount of PCR product while the 1.8 and 2.0 mM $MgCl_2$ with 237.5 µM dNTPs produced a large amount of PCR product. This indicates that the amount of PCR product in this experiment is related to the dNTP and not the $MgCl_2$ concentration. No PCR product was generated with the Fd or CH2/CH3 primers under the conditions used.

Example 2

Primer Extension Reactions with 3' Mismatched Primers

These experiments investigated the ability of Taq and Pfu DNA polymerases both together and in separate reactions to extend from primers which contain one or two 3' mismatches. The first experiment demonstrates that Taq DNA polymerase can only extend from a primer which matches at the 3' end under the conditions used (2.1 and 6.1 mM $MgCl_2$). The next experiment demonstrates that Taq and Pfu DNA polymerases used in the same reaction will extend from all the primers with 3' mismatches that were used from both hybridoma and PBL templates while neither polymerase alone was able to extend from all primers. The combination of both polymerases also resulted in more product in some of the samples.

This series of experiments suggest that Taq in Taq buffer will extend from a primer that is perfectly matched at the 3' end, in V25 buffer will extend from a primer that has one T which creates a mismatch at the 3' end of a primer, and in V25 buffer will not extend from a primer that has two Ts which create two mismatches at the 3' end of a primer. Taq and Pfu DNA polymerases in V25 buffer will extend from a primer that has two Ts which create a mismatch at the 3' end of a primer.

It was also speculated that Taq and Pfu DNA polymerases may complement each other in the reaction by polymerizing through A:T or G:C rich regions of a template where one enzyme could not polymerize well through both types of regions. The Pfu genome is 38% GC while the Taq genome is 66.8% GC.

Taq DNA Polymerase with 9F12 Template

The ability of Taq DNA polymerase to extend from primers with one or more mismatches at the 3' end was investigated. Nucleotide sequences of the 5' primers based on the AB-61 primer and used to amplify 9F12 cDNA are given in Table 12. The 3' primer in reactions which amplified the Fd portion of the human heavy chain was AB-76. The 3' primer in reactions which amplified the VH portion of the human heavy chain was MK-39. The light chain 5' VL primer was AB-25 and the 3' CL primer was AB-94.

9F12 cDNA template was generated by isolating total RNA from the hybridoma cells using an RNA isolation kit (Stratagene). mRNA is converted to cDNA in a first strand synthesis reaction using an oligo-dT primer for the light chain and AB-76 for the heavy chain. The first strand reactions was performed as described above except 200 units of Superscript (BRL; Gaithersburg, Md.)] was substituted for M-MLVRT and the reactions were incubated at 42° C. for 1 hour.

PCR reactions were at a primer concentration of 0.2 μM of each 5' and 3' primer in 1× Taq buffer (Table 17) with either 2.1 or 6.1 mM $MgCl^2$, 175 μM each dNTP and 2.5 units Taq DNA polymerase using 1/10 of the cDNA prepared in the first strand reaction as the template. Samples were denatured at 95° C. for 5 minutes and annealed at 54° C. for 5 minutes followed by PCR amplification at 72° C. for 3 minutes, 93° C. for 1.5 minutes and 54° C. for 2.5 minutes for 40 cycles. Samples were analyzed as described above and the results are given in Table 3.

TABLE 3

Taq DNA polymerase with 9F12 template

| | | Taq in Taq buffer | |
|---|---|---|---|
| primers | product | 2.1 mM $MgCl_2$ | 6.1 mM $MgCl_2$ |
| AB-61/AB-76 | Fd | 2+ | − |
| AB-714/AB-76 | Fd | − | − |
| AB-715/AB-76 | Fd | − | − |
| AB-716/AB-76 | Fd | − | − |
| AB-717/AB-76 | Fd | − | − |
| AB-61/MK-39 | VH | 2+ | + |

PCR products of the appropriate size were generated only when AB-61 was used as the 5' primer. None of the 3' mismatched primers generated a PCR product of the appropriate size although many unappropriately sized products were made. Fd and VH products were generated in the reaction containing 2.1 mM $MgCl_2$ while only the VH was produced in the reaction containing 6.1 mM $MgCl_2$.

These results suggested that Taq DNA polymerase was not able to extend from 3' mismatched primers under the conditions used and that increasing the $MgCl_2$ concentration did not result in either an increase in PCR product, the ability to extend from 3' mismatched primers, or generation of PCR products not made with 2.1 mM $MgCl_2$.

Taq and Pfu DNA Polymerases with 9F12 and PBL Templates

The next experiment investigated the effect of using Pfu and Taq DNA polymerases in the same PCR reaction to extend from primers with 3' matches and mismatches. The same primers were used (MK-205 which has the same 21 bp on the 3' end as AB-61 was substituted for AB-61) as described above to amplify Fd, VH, CH1, and LC from PBL and 9F12 cDNAs. PCR reactions were performed in 1× V25 buffer (Table 17) with 200 μM each dNTP and 2.5 units of both Taq and Pfu DNA polymerases or with Pfu DNA polymerase alone using cDNA generated as described above from 9F12 & PBL RNA as the template. Samples were denatured at 94° C. for 5 minutes and annealed at 47° C. for 5 minutes followed by PCR amplification at 71° C. for 3 minutes, 92° C. for 1 minute and 47° C. for 2.5 minutes for 5 cycles and 71° C. for 3 minutes, 92° C. for 1 minute and 51° C. for 2.5 minutes for 35 cycles. The lower annealing temperatures were used to try to improve primer:template annealing when mismatches occurred. Samples were analyzed as described above and the results are given in Tables 4 and 5.

TABLE 4

Taq and Pfu DNA polymerases with 9F12 and PBL templates
V25 buffer

| | 9F12 template | | PBL template | |
|---|---|---|---|---|
| | Pfu/Taq | | | Pfu |
| primers | Fd | VH | Fd | VH |
| AB-61/AB-76 | 5+ | 5+ | + | +/− |
| AB-714/AB76 | 5+ | 5+ | 2+ | +/− |
| AB-715/AB76 | 2+ | 5+ | +/− | +/− |
| AB-716/AB76 | 5+ | 5+ | 2+ | +/− |
| AB-717/AB76 | 5+ | 5+ | + | +/− |

TABLE 5

| | | 9F12 templates | | PBL templates | |
|---|---|---|---|---|---|
| | | Pfu/Taq | | | Pfu |
| primers | product | Fd | VH | Fd | VH |
| MK-94/AB-76 | CH1 | 5+ | | +/− | +/− |
| AB-25/AB-94 | LC | +/− | | +/− | +/− |

An unexpected result in this experiment was that more amplification product was generated when Taq and Pfu DNA polymerases were used in the same PCR reaction in V25 buffer with both 9F12 and PBL cDNA as the template. Numerous previous experiments using identical first strand synthesis and PCR conditions with Taq DNA polymerase had resulted in only a very small amount of Fd product generated from the same PBL mRNA. A very small amount of VH and CH1 products were generated using Pfu DNA polymerase alone in V25 buffer with PBL cDNA as a template.

Significant amounts of both Fd and VH PCR products were generated with 9F12 cDNA as a template with all of the 5' primers, including the 3' mismatched primers (AB-714 to AB-717), when both Taq and Pfu DNA polymerases were used. This contrasted with the previous experiment when Taq DNA polymerase was not able to extend from the 3' mismatched primers (AB-714 through AB-717) under the conditions used. These results suggested that Pfu DNA polymerase can remove 1–2 mismatched bases from the 3' end of the primer. This would enable either Pfu or Taq DNA polymerase to extend from the perfectly base paired primer: template.

Taq and Pfu DNA Polymerases with 9F12 and PBL Templates

The above experiment was repeated to verify the results. The same primers were used to amplify Fd, CH1, and LC using PBL and 9F12 cDNAs as templates. PCR reactions were performed in V25 buffer (Table 17) with 200 μM each dNTP and 2.5 units of both Taq and Pfu DNA polymerases either together in the same reaction and or in separate reactions. PCR conditions were the same as described above and the results are given in Table 5.

TABLE 6

Taq and Pfu DNA Polymerases with 9F12 and PBL Templates

| | | V25 buffer | | | | | |
|---|---|---|---|---|---|---|---|
| | | 9F12 template | | | PBL template | | |
| primers | product | Taq | Pfu | Pfu/Taq | Taq | Pfu | Pfu/Taq |
| AB-61/AB-76 | Fd | — | — | + | — | + | — |
| AB-714/AB-76 | Fd | 3+ | — | 4+ | + | — | 3+ |
| AB-715/AB-76 | Fd | — | — | 2+ | — | — | + |
| AB-716/AB-76 | Fd | 4+ | — | 4+ | 3+ | + | + |
| AB-717/AB-76 | Fd | 2+ | — | 4+ | + | — | 3+ |
| MK94/AB-76 | CH1 | 4+ | 4+ | 4+ | 3+ | — | — |
| AB-25/AB-94 | LC | 2+ | — | — | + | — | — |

PCR products generated with Pfu were Fd with MK-205 from PBL template and CH1 from 9F12 template. PCR products generated with Taq were Fd with AB-714, AB-716, AB-717, CH1, and LC with PBL template and Fd with AB-714, AB-716, AB-717, CH1 and LC with 9F12 template. PCR products generated with Pfu and Taq were Fd with MK-205, AB-714, AB-717 and a very small amount with AB-715 and AB-716 from PBL template. PCR products generated with Pfu and Taq were Fd with AB-714, AB-715, AB-716, AB-717 and CH1 from 9F12 template.

The amount of PCR product varied, however, in general more product was generated with the 9F12 template than with the PBL template. This may be due to the heterogeneity of the PBL template when compared to the homogeneity of the 9F12 hybridoma template. When a homogeneous template is amplified and the strand is not completed, it may anneal to its template in a subsequent round of amplification and be extended to full length. When a heterogeneous template is amplified and the strand is not complete, the chances of it annealing to its original template in a subsequent round of amplification will be related to the heterogeneity of the templates present but will be less than that of a homogeneous template. This may help explain why homogeneous templates produce more PCR product than heterogenous templates.

In this experiment Taq DNA polymerase was able to extend from the 3' mismatched primers which contain only a single mismatched base (AB-714, AB-716, and AB-717) but not one that has two mismatched bases (AB-715) with both the PBL and 9F12 cDNA templates. In a previous experiment, Taq DNA polymerase was not able to do this, however, these results are consistent with the results of Kwok, et al. (1990, supra). Both AB-715 and AB-717 contain 2 dTTPs at the 3' end of the primer but in different positions. AB-715 replaces the last two dGTPs on the 3' end and AB-717 replaces the last dGTP and adds a dTTP to the 3' end. Because the corresponding base in the template is not known, the 3' dTTP in AB-717 may not create a mismatch with the template.

The V25 buffer used in this experiment had been made incorrectly and was 5 mM KCl instead of 10 mM KCl. KCl concentration has been shown to effect processivity and/or activity of Taq. This was corrected for all future experiments.

Example 3

Effect of Different Ratios of Taq and Pfu DNA Polymerases on Extension from 3' Mismatched Primers This experiment investigated different ratios of Taq and Pfu DNA polymerases and template concentrations when amplifying from perfectly matched and 3' mismatched primers. Plasmid DNA which encoded an anti-tetanus toxoid immunoglobulin fragment (kappa light chain and Fd portion of the heavy chain) was used as the template (Mullinax et al. 1990, supra). Although optimal polymerase ratios and template concentrations were not identified in these experiments, additional experimentation would need to be done before concluding that they did not have an effect.

Effect of Pfu DNA Polymerase Ratio on Extension from 3' Mismatched Primers

Five different ratios of Taq and Pfu DNA polymerases were used in PCR reactions with a combined total of 2.5 units per reaction. The ratios were 9:1, 7:3, 5:5, 3:7, and 1:9 of Taq:Pfu. The Fd primers were AB-61, AB-715, and AB-717 in V25 buffer. Anti-tetanus toxoid plasmid DNA encoding a kappa LC and Fd was used as the template. Samples were denatured at 95° C. for 7 minutes and annealed at 40° C. for 7–10 minutes followed by PCR amplification at 72° C. for 2 minutes, 95° C. for 1 minute and 50° C. for 2 minutes for 30 cycles. Samples were analyzed as described above and results are given below.

TABLE 7

EFFECT OF DIFFERENT RATIOS OF TAQ AND PFU DNA POLYMERASES ON EXTENSION FROM 3' MISMATCHED PRIMERS

| | | ratio of Taq:Pfu DNA polymerases | | | | | | |
|---|---|---|---|---|---|---|---|---|
| primers | product | 10:0 | 9:1 | 7:3 | 5:5 | 3:7 | 1:9 | 0:10 |
| AB-61/AB-76 | Fd | 4+ | 5+ | 5+ | 5+ | 5+ | 4+ | 4+ |
| AB-715/AB-76 | Fd | — | 5+ | 5+ | 5+ | 5+ | 2+ | 5+ |
| AB-717/AB-76 | Fd | 2+ | 5+ | 5+ | 5+ | 5+ | 5+ | 5+ |

All PCR reactions generated a significant amount of PCR product with little variation except the reactions with AB-715 and AB-717 with Taq DNA polymerase alone and the reaction with Taq:Pfu at 1:9 with AB-715. All of the reactions which combine both Taq and Pfu DNA polymerases or contain Pfu alone produced a significant amount of product. Taq DNA polymerase alone not would be expected to extend efficiently from the 3' mismatched primers.

Template concentration can affect the amplification efficiency and may explain there is little difference in the amount of PCR product in the different samples when the ratio of DNA polymerases is varied. In the next experiment, three different template concentrations were used to try to determine the effect of template concentration.

Effect of Template Concentration

Template concentrations were 100, 50, and 10 nanograms per reaction with either 2.5 units of Taq or Pfu DNA polymerase in the reaction in V25 buffer. The Fd primers were AB-61, AB-715, and AB-717 in V25 buffer. Samples were denatured at 95° C. for 7 minutes and annealed at 40° C. for 7–10 minutes followed by PCR amplification at 72° C. for 2 minutes, 95° C. for 1 minute and 50° C. for 2 minutes for 30 cycles. Samples were analyzed as described above and results are given in Table 8.

TABLE 8

EFFECT OF TEMPLATE CONCENTRATION

| | | \multicolumn{6}{c}{template concentration} | | | | | |
|---|---|---|---|---|---|---|---|
| | | 100 ng | | 50 ng | | 10 ng | |
| primers | product | Taq | Pfu | Taq | Pfu | Taq | Pfu |
| AB-61/AB-76 | Fd | 5+ | 5+ | 5+ | 5+ | 5+ | 5+ |
| AB-715/AB-76 | Fd | 5+ | 5+ | 5+ | 5+ | 5+ | 5+ |
| AB-717/AB-76 | Fd | 5+ | 5+ | 5+ | 5+ | 5+ | 2+ |

Varying the template concentration did not seem to have an effect on the amount of PCR template generated except in the 10 ng template sample with Pfu DNA polymerase alone with AB-717. The results seen previously with AB-715 where there was no amplification with Taq DNA polymerase alone was not reproduced and the experimenter indicated that an error could have been made. The experiment with AB-715 alone was repeated.

This experiment repeated the experiment described above using just the AB-715 primer under the same conditions. Samples were analyzed and described above and results are given in Table 9.

TABLE 9

EFFECT OF TEMPLATE CONCENTRATION

| | | \multicolumn{6}{c}{template concentration} | | | | | |
|---|---|---|---|---|---|---|---|
| | | 100 ng | | 50 ng | | 10 ng | |
| primer | product | Taq | Pfu | Taq | Pfu | Taq | Pfu |
| AB-715/AB-76 | Fd | 4+ | 3+ | 3+ | 2+ | 1+ | 5+ |

The amount of PCR product generated correlated with template concentration in the reactions with Taq DNA polymerase alone and may indicate that the template concentration affects amplification efficiency from mismatched primers. No consistent effect could be correlated with Pfu DNA polymerase.

Example 4

Effect of Annealing Temperature on Extension from 3' Mismatched Primers

The next experiment compared Taq and Taq with Pfu in Taq and V25 buffers with mismatched primers at different annealing temperatures. This experiment demonstrates that more PCR product is generated from a perfectly matched primer at a lower annealing temperature than at a higher temperature. No product was produced with the primer with 2 mismatches under any of the conditions used.

Effect of Annealing Temperatures of Extension from 3' Matched and Mismatched Primers Taq and Taq with Pfu in Taq and V25 buffers with mismatched primers were extended at different annealing temperatures. The Fd primers were AB-61 and AB-715. cDNA templates were prepared from PBLs and 9F12. Samples were denatured at 95° C. for 5 minutes and annealed at either 48° C. or 52° C. for 5 minutes followed by PCR amplification at 71° C. for 3 minutes, 92° C. for 1 minute and 48° C. or 52° C. for 2.5 minutes for 5 cycles and 71° C. for 3 minutes, 92° C. for 1 minute and 54° C. for 2.5 minutes for 40 cycles. The lower annealing temperatures were used determine the effect the lower temperature had on primer:template annealing when mismatches occurred. Samples were analyzed as previously described and results are given in Table 10.

TABLE 10

Effect of Annealing Temperatures on Extension From 3' Matched and Mismatched Primers

| | | \multicolumn{4}{c}{9F12 template} | | | | \multicolumn{4}{c}{PBL template} | | | |
|---|---|---|---|---|---|---|---|---|---|
| | | Taq buffer | | V25 buffer | | Taq buffer | | V25 buffer | |
| primers | product | Taq | Pfu/Taq | Taq | Pfu/Taq | Taq | Pfu/Taq | Taq | Pfu/Taq |
| | | \multicolumn{8}{c}{annealing at 48° C. (×5 cycles) and 52° C. (×35 cycles)} | | | | | | | | |
| AB-61/AB-76 | Fd | 4+ | 4+ | 4+ | 4+ | +/− | + | — | +/− |
| AB-715/AB-76 | Fd | — | — | — | — | — | — | — | — |
| | | \multicolumn{8}{c}{annealing at 54° C. (×40 cycles)} | | | | | | | | |
| AB-61/AB-76 | Fd | 4+ | 4+ | 2+ | + | — | — | — | — |
| AB-715/AB-76 | Fd | — | — | — | — | — | — | — | — |

PCR products generated with Pfu and Taq in Taq or V25 buffers were a very small amount of Fd using AB-61 with the PBL template at the lower and not the higher annealing temperature. PCR products generated with Taq with and without Pfu in Taq or V25 buffer using AB-61 with the 9F12 template resulted in more product at the lower rather than the higher annealing temperature. No PCR products were generated with the AB-715 primer in any samples.

Results indicated that none of the polymerases or buffer combinations tested extended from the AB-715 primer. AB-61 and AB-715 differ by the deletion of two dGTPs and the addition of two dTTPs at the 3' end (Table 13). The lower annealing temperatures did produce either the presence of or an increase in the amount of PCR product generated.

Example 5

PCR Reactions Using Primers without 3' Mismatches

The object of the experiments with the 3' mismatched primers was to determine PCR conditions would result in a sufficient amount of high fidelity PCR product to enable cloning of the encoded immunoglobulin fragments. Therefore, the original PCR primers designed to amplify all human heavy chain genes were now used in the PCR reactions with Taq and Pfu DNA polymerases separately and in the same reaction. Results indicate that there was no significant difference in the amount of PCR product generated when either Taq or Taq and Pfu DNA polymerases were used in these experiments.

Taq and Pfu DNA Polymerases with 9F12 and PBL Templates

The first strand synthesis and PCR reactions were performed as described above under PCR REACTIONS WITH 3' MISMATCHED PRIMERS—Taq and Pfu DNA polymerases with 9F12 and PBL templates with the following change. AB-61, AB-62, AB-63, and AB-64 (Table 18) were used as the 5' VH primers. Samples were analyzed as described above and results are given in Table 11.

TABLE 11

Taq and Pfu DNA Polymerases With 9F12 and PBL Templates

| | | V25 buffer | | | | | |
| | | 9F12 template | | | PBL template | | |
| primers | product | Taq | Pfu | Pfu/Taq | Taq | Pfu | Pfu/Taq |
|---|---|---|---|---|---|---|---|
| AB-61/AB-76 | Fd | 4+ | — | — | 4+ | +/− | 4+ |
| AB-62/AB-76 | Fd | 4+ | — | 4+ | 4+ | +/− | 4+ |
| AB-63/AB-76 | Fd | 4+ | + | 4+ | +/− | — | — |
| AB-64/AB-76 | Fd | 4+ | — | 4+ | 2+ | — | 2+ |
| MK-94/AB-76 | CH1 | 4+ | 3+ | 4+ | 2+ | — | 3+ |
| AB-25/AB-94 | LC | 2+ | — | 3+ | — | — | + |

PCR products generated with Pfu were a very small amount of Fd with AB-61 and AB-62 from PBL template and Fd with AB-63 and CH1 from 9F12 template. PCR products generated with Taq were Fd with all 5' primers and CH1 PBL and 9F12 templates and LC with 9F12 template. PCR products generated with Pfu and Taq were Fd with AB-61, AB-62, AB-64, CH1, and LC from PBL template. PCR products generated with Pfu and Taq were Fd with AB-62, AB-63, AB-64, CH1, and LC from 9F12 template. In general, the results with the PBL template had a lot of failure products and there was significantly more product with the 9F12 template.

The inability of Pfu DNA polymerase to extend from any of the 5' primers other than AB-63 may be due to internal mismatches with 9F12 as the template and not be due to the 3' primer:template mismatches.

Example 6

The effect of a combination of four different polymerases in seven different buffers was tested on three different templates. The desired effects were an increase in the amount of PCR product generated and/or an increased specificity of amplification. No effect was observed between using a combination of four polymerases and Taq DNA polymerase in the buffers tested.

Seven different templates with eight different primer sets were used in this experiment. The genomic DNAs were isolated from human, Epstein Barr virus, *Escherichia coli*, and transgenic and normal mouse. Plasmid DNAs were pBluescript II and pBluescript containing the light chain and Fd of an anti-tetanus toxoid immunoglobulin (Mullinax et al., 1990, supra). Primer sequences and their respective DNA templates are given in Table 16. The thermostable polymerases used in this experiment were Taq, Exo⁺ and Exo⁻ Pfu, and ES-4 DNA polymerases (Stratagene; La Jolla, Calif.) at final concentrations of 2.5, 1.25, 1.25, and 0.125 units per reaction, respectively. PCR reactions were at a primer concentration of 0.2 μM of each 5' and 3' primer in 1× Taq buffer, 1× Pfu #1, or 1× Pfu #3 (Table 17) with 200 μM each dNTP. An additional reaction with Taq DNA polymerase in 1× Taq buffer was also performed. Samples were denatured at 95° C. for 5 minutes and annealed at 40° C. for 5 minutes followed by PCR amplification at 95° C. for 0.5 minutes, 40° C. for 1.5 minutes and 68° C. for 3 minutes for 25 cycles. Samples were analyzed as previously described and results are not given.

Results indicated that no significant increase in the amount of PCR product generated or an increase in specificity was observed when comparing Taq DNA polymerase in Taq buffer and a combination of polymerases in the three different buffers tested. Results seemed to correlate with the buffer used and not the polymerase.

Example 7

Taq and Pfu DNA Polymerases in Splice Overlap Extension Reactions to Generate Cloning Vectors A series of lambda-based vectors were constructed to express immunoglobulin fragments on the surface of M13 phage. The example described below describes the construction of one of these vectors. Pfu and Taq DNA polymerases in combination were used to construct this vector because of the high processivity of Taq DNA polymerase and the high fidelity of Pfu DNA polymerase. The nucleotide sequence of the cpVIII expression vector matched the expected nucleotide sequence.

cpVIII Expression Vector Construction

Oligonucleotide primers used to construct the IZ H-8 (−1 to 50) vector with the cpVIII protein domain were designed to encode the following: an Xho I restriction site, stop codons, nucleotide spacer sequences, an Xba I site that generates an amber codon, amino acids −1 to 50 of cpVIII, stop codons, and a Spe I restriction site.

Nucleotide sequences of the primers used to amplify cpVIII from M13 Phagescript DNA (Stratagene; La Jolla, Calif.) using the 5' and 3' cpVIII primers are given in Table 19. All PCR reactions were at a primer concentration of 0.2 μM of each 5' and 3' primer in 1× V25 buffer with 200 μM each dNTP and 2.5 units each Taq and Pfu DNA polymerases. Samples were denatured at 95° C. for 5 minutes and annealed at 54° C. for 5 minutes followed by PCR amplification at 74° C. for 3 minutes, 93° C. for 1.5 minutes and 54° C. for 2.5 minutes for 30 cycles.

The cpVIII encoding PCR product was restriction digested with Xho I and Spe I and ligated into the IZ H vector (Stratacyte; La Jolla, Calif.; Huse, W. D., L. Sastry, S. A. Iverson, A. S. Kang, M. Alting-Mees, D. R. Burton, S. J. Benkovic, and R. A. Lerner. Generation of a large combinatorial library of the immunoglobulin repertoire in phage lambda. 1989. *Science*. 246:1275–1281) which had previously been restriction digested with Xho I and Spe I. The ligation products were packaged with Gigapack II® Gold (Stratagene; La Jolla, Calif.) and plated with XL1-Blue host cells. The desired construct was identified by PCR amplification of isolated phage cores with the 5' and 3' cpVIII cloning primers, converted to the plasmid format by in vivo excision with VCS M13 helper phage (Short, J., J. M Fernandez, J. A. Sorge, and W. D. Huse, Lambda ZAP: a bacteriophage lambda vector with in vitro excision proprietes, 1988, *Nucleic Acids Res.* 16:7583–7600) and the nucleotide sequence was determined by the dideoxy method. The nucleotides was sequence as expected.

TABLE 12

HUMAN HEAVY CHAIN PCR PRIMERS
WITH MATCHED AND 3' MISMATCHES VH PRIMERS

| primer description | nucleotide sequence (5' to 3') |
|---|---|
| AB-205 5' VH | GTCCTGTCCGAGGTGCAGCTGCTCGAGTCTGG (SEQ ID NO:1) |
| AB-61 5' VH | AGGTGCAGCTGCTCGAGTCTGG (SEQ ID NO:2) |

TABLE 12-continued

HUMAN HEAVY CHAIN PCR PRIMERS
WITH MATCHED AND 3' MISMATCHES VH PRIMERS primer description nucleotide sequence (5' to 3')

AB-714 5' VH      AGGTGCAGCTGCTCGAGTCTGT
                  (SEQ ID NO:3)

AB-715 5' VH      AGGTGCAGCTGCTCGAGTCTTT
                  (SEQ ID NO:4)

AB-716 5' VH      AGGTGCAGCTGCTCGAGTCTGGT
                  (SEQ ID NO:5)

AB-717 5' VH      AGGTGCAGCTGCTCGAGTCTGTT
                  (SEQ ID NO:6)

AB-76  3' CH1     AGCATCACTAGTACAAGATTTGGGCTC
                  (SEQ ID NO:7)

AB-52  3' CH1     CGGGAGATCATGAGGGTGTCCTT
                  (SEQ ID NO:8)

MK-39  3' VH      ATATACTAGTGAGACAGTGACCAGGGTTCCTT
                  GGCCCCA
                  (SEQ ID NO:9)

TABLE 13

HUMAN HEAVY AND LIGHT CHAIN PCR PRIMERS primer description nucleotide sequence (5' to 3')

AB-205 5' VH      GTCCTGTCCGAGGTGCAGCTGCTCGAGTCTGG
                  (SEQ ID NO:1)

AB-61  5' VH      AGGTGCAGCTGCTCGAGTCTGG
                  (SEQ ID NO:2)

AB-714 5' VH      AGGTGCAGCTGCTCGAGTCTGT
                  (SEQ ID NO:3)

AB-715 5' VH      AGGTGCAGCTGCTCGAGTCTTT
                  (SEQ ID NO:4)

AB-716 5' VH      AGGTGCAGCTGCTCGAGTCTGGT
                  (SEQ ID NO:5)

AB-717 5' VH      AGGTGCAGCTGCTCGAGTCTGTT
                  (SEQ ID NO:6)

AB-76  3' CH1     AGCATCACTAGTACAAGATTTGGGCTC
                  (SEQ ID NO:7)

AB-52  3' CH1     CGGGAGATCATGAGGGTGTCCTT
                  (SEQ ID NO:8)

MK-39  3' VH      ATATACTAGTGAGACAGTGACCAGGGTTCCTT
                  GGCCCCA
                  (SEQ ID NO:9)

AB-25  5' VL      GTGCCAGATGTGAGCTCGTGATGACCCAGTCT
                  CCA
                  (SEQ ID NO:10)

AB-94  3' CL      TCCTTCTAGATTACTAACACTCTCCCCTGTTG
                  AAGCTCTTTGTGACGGGCGAACTC
                  (SEQ ID NO:11)

TABLE 13-continued

HUMAN HEAVY AND LIGHT CHAIN PCR PRIMERS primer description nucleotide sequence (5' to 3')

MK-94  5' CH1    GTCTCACTAGTCTCCACCAAGGGCCCATCG
                 GTC
                 (SEQ ID NO:12)

AB-58  3' CH2    CGGGAGATCATGAGGGTGTCCTT
                 (SEQ ID NO:13)

MK-25  5' CH2    CTCAGTATGGTGGTTGTGC
                 (SEQ ID NO:14)

MK-26  3' CH3    CCGGAATTCTTATCATTTACCCGGAGA
                 (SEQ ID NO:15)

*nucleotides in bold indicate where dTTP was introduced into the AB-61 primer

TABLE 14 pBluescript PCR primers description    nucleotide sequence (5' to 3')

T3             ATTAACCCTCACTAAAG
               (SEQ ID NO:16)

T7             AATACGACTCACTATAG
               (SEQ ID NO:17)

TABLE 15

MOUSE HEAVY AND LIGHT CHAIN PCR PRIMERS primer description    nucleotide sequence (5' to 3')

AB-25  5' VL kappa    GTGCCAGATGTGAGCTCGTGATGACCCAGTC
                      TCCA
                      (SEQ ID NO:10)

AB-26  3' CL kappa    TCCTTCTAGATTACTAACACTCTCCCCTGTT
                      GAA
                      (SEQ ID NO:18)

AB-28  5' VL lambda   CTGCACAGGGTCCTGGGCCGAGCTCGTGGTG
                      ACTCAG
                      (SEQ ID NO:19)

AB-92  3' VL lambda   GCATTCTAGACTATTAACATTCTGTAGGGGC
                      (SEQ ID NO:20)

AB-19  5' VH          AGGTCCAGCTGCTCGAGTCTGG
                      (SEQ ID NO:21)

AB-41  3' CH1         AGGCTTACTAGTACAATCCCTGGGCACAAT
                      (SEQ ID NO:22)

MK-501 3' VH          CCGTTACTAGTAGCCAAAACGACACCCCCAT
                      CTGTC
                      (SEQ ID NO:23)

TABLE 16

DNA TEMPLATES AND PCR PRIMER SEQUENCES

| template description | primer description | nucleotide sequence (5' to 3') |
|---|---|---|
| human | 5' Gaucher's disease | CCTGAGGGCTCCCAGAGAGTGG (SEQ ID NO:24) |
| human | 3' Gaucher's disease | GGTTTAGCACGACCACAACAGC (SEQ ID NO:25) |
| pBluescript KS+ | 5' multiple cloning site | ATTAACCCTCACTAAA (SEQ ID NO:26) |
| pBluescript KS+ | 3' multiple cloning site | AATACGACTCACTATAG (SEQ ID NO:27) |
| Epstein Barr virus | 5' nuc antigen gene | GGCTGGTGTCACCTGTGTTA (SEQ ID NO:28) |
| Epstein Barr virus | 3' nuc antigen gene | CCTTAGGAGGAACAAGTCCC (SEQ ID NO:29) |
| E. coli | 5' RNase H gene | CTTGAAGATCTATGCTTAAACAGGTAG (SEQ ID NO:30) |
| E. coli | 3' RNase H gene | CATGTGAATTCTTAAACTTC (SEQ ID NO:31) |
| transgenic mouse | 5' lambda lacZ insert | GGTGGCGACGACTCCTGGAGCCC (SEQ ID NO:32) |
| transgenic mouse | 3' lambda lacZ insert | GACAGTCACTCCGGCCCGTGCGG (SEQ ID NO:33) |
| human | 5' fucosidase gene | AAGCTTCAGGAAAACAGTGAGCAGCGCCTC (SEQ ID NO:34) |
| human | 3' fucosidase gene | ACTCAGGTATCTTTGACAGT (SEQ ID NO:35) |
| nontransgenic mouse | 5' B-adrenergic receptor | GGAATTCGTAACAGCACTTACGGTAGC (SEQ ID NO:36) |
| nontransgenic mouse | 3' B-acrenergic receptor | AGCACTCATAAGTGACACCC (SEQ ID NO:37) |
| transgenic mouse | 5' lambda lacI insert | CATAGCGAATTCGCAAAACCTTTCGCGGTATGG (SEQ ID NO:38) |
| transgenic mouse | 3' lambda lacI insert | ACTACGGAATTCCACGGAAAATGCCGCTCATCC (SEQ ID NO:39) |

TABLE 17

10x PCR BUFFER COMPONENTS

| component | Taq | V25 | Pfu #1 | Pfu #3 |
|---|---|---|---|---|
| KCl | 500 mM | 100 mM | 100 mM | 100 mM |
| (NH4)2SO4 | | 60 mM | 60 mM | 100 mM |
| tris-Cl, pH 8.8 | 100 mM | | | |
| tris-Cl, pH 8.2 | | 200 mM | 200 mM | |
| tris-Cl, pH 8.5 | | | | 200 mM |
| MgCl2 | 15 mM | 15 mM | 20 mM | 15 mM |
| MgSO4 | | | | 20 mM |
| Triton X-100 | | 1%(v/v) | 1%(v/v) | 1%(v/v) |
| bovine serum albumin | | 100 µg/ml | 100 µg/ml | 1 mg/ml |
| gelatin | 0.01% (w/v) | | | |

TABLE 18

HUMAN VH PCR PRIMERS

| primer | description | nucleotide sequence (5' to 3') |
|---|---|---|
| AB-61 | 5' VH | AGGTGCAGCTGCTCGAGTCTGG (SEQ ID NO:2) |
| AB-62 | 5' VH | AGGTGCAGCTGCTCGAGTCGGG (SEQ ID NO:40) |
| AB-63 | 5' VH | AGGTGCAACTGCTCGAGTCTGG (SEQ ID NO:41) |
| AB-64 | 5' VH | AGGTGCAACTGCTCGAGTCGGG (SEQ ID NO:42) |

TABLE 19

OLIGONUCLEOTIDE PRIMERS USED TO CONSTRUCT THE IZ H-8 (−1 to 50) VECTOR

| | | |
|---|---|---|
| 5' cpVIII | TTGACTCGAGTAATCTGAGCTAAAGTCTAGAGCGCTGAGGGTGACGATCC (SEQ ID NO:43) | |
| 3' cpVIII | ATGGCAACTAGTTATCAGCTTGCTTTCGAGG (SEQ ID NO:44) | |

EQUIVALENTS

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The foregoing written specification is considered to be sufficient to enable one skilled in the art to practice the invention. Indeed, various modifications of the above-described modes for carrying out the invention which are obvious to those skilled in the field of molecular biology or related fields are intended to be within the scope of the following claims.

What is claimed is:

1. A kit for the synthesis of a polynucleotide, said kit comprising:

a composition comprising:

(a) a first DNA polymerase, wherein said first polymerase possesses 3'–5' exonuclease activity and is thermostable, and (b) a second DNA polymerase, wherein said second polymerase substantially lacks 3'–5' exonuclease activity and is thermostable;

wherein both the first DNA polymerase and the second DNA polymerase retain at least 50 percent of their specific activity after exposure to a temperature of 80 degrees Celsius for a period of 20 minutes.

2. A method of amplifying a polynucleotide sequence, said method comprising mixing a composition with a synthesis primer and a synthesis template, said composition comprising (a) a first DNA polymerase possessing 3'–5' exonuclease activity, wherein said first polymerase is thermostable, and (b) a second DNA polymerase, wherein said second polymerase substantially lacks 3'–5' exonuclease activity and is thermostable;

wherein both the first DNA polymerase and the second DNA polymerase retain at least 50 percent of their specific activity after exposure to a temperature of 80 degrees Celsius for a period of 20 minutes.

3. A method according to claim 2, wherein said first DNA polymerase is selected from the group consisting of *Pyrococcus furiosus* DNA polymerase, *Thermotoga maritima* DNA polymerase, *Thermococcus litoralis* DNA polymerase, and *Pyrococcus* GB-D DNA polymerase.

4. A method according to claim 3, wherein said first DNA polymerase is *Pyrococcus furiosus* DNA polymerase.

5. A method according to claim 2, wherein the second DNA polymerase is selected from the group consisting of *Thermus aquaticus* DNA polymerase, (exo–) *Thermococcus*

*litoralis* DNA polymerase, (exo–) *Pyrococcus furiosus* DNA polymerase, and (exo–) *Pyrococcus* GB-D DNA polymerase.

6. A method according to claim 2, wherein said second DNA polymerase is *Thermus aquaticus* DNA polymerase.

7. A method according to claim 4, wherein said second DNA polymerase is *Thermus aquaticus* DNA polymerase.

8. A kit according to claim 1, wherein said first DNA polymerase is selected from the group consisting of *Pyrococcus furiosus* DNA polymerase, *Thermotoga maritima* DNA polymerase, *Thermococcus litoralis* DNA polymerase, and *Pyrococcus* GB-D DNA polymerase.

9. A kit according to claim 8, wherein said first DNA polymerase is *Pyrococcus furiosus* DNA polymerase.

10. A kit according to claim 1, wherein the second DNA polymerase is selected from the group consisting of *Thermus aquaticus* DNA polymerase, (exo–) *Thermococcus litoralis* DNA polymerase, (exo–) *Pyrococcus furiosus* DNA polymerase, and (exo–) *Pyrococcus* GB-D DNA polymerase.

11. A kit according to claim 10, wherein said second DNA polymerase is *Thermus aquaticus* DNA polymerase.

12. A kit according to claim 1, said kit further comprising DNA primers.

13. A composition comprising:
(a) a first DNA polymerase, wherein said first polymerase possesses 3'–5' exonuclease activity and is thermostable, and
(b) a second DNA polymerase, wherein said second polymerase substantially lacks 3'–5' exonuclease activity and is thermostable;
wherein both the first DNA polymerase and the second DNA polymerase retain at least 50 percent of their specific activity after exposure to a temperature of 80 degrees Celsius for a period of 20 minutes.

14. A composition according to claim 13, wherein said second DNA polymerase is *Thermus aquaticus* DNA polymerase.

15. A composition according to claim 13, wherein said first DNA polymerase is selected from the group consisting of *Pyrococcus furiosus* DNA polymerase, *Thermotoga maritima* DNA polymerase, *Thermococcus litoralis* DNA polymerase, and *Pyrococcus* GB-D DNA polymerase.

16. A composition according to claim 14, wherein said first DNA polymerase is *Pyrococcus furiosus* DNA polymerase.

17. A composition according to claim 15, wherein said first DNA polymerase is *Thermococcus litoralis* DNA polymerase.

18. A composition according to claim 15, wherein said first DNA polymerase is *Pyrococcus* GB-D DNA polymerase.

19. A composition according to claim 15, wherein said first DNA polymerase is *Thermotoga maritima* DNA polymerase.

20. A composition according to claim 17, wherein the second DNA polymerase is *Thermus aquaticus* DNA polymerase.

21. A composition according to claim 17, wherein the second DNA polymerase is (exo–) *Thermococcus litoralis* DNA polymerase.

22. A composition according to claim 17, wherein the second DNA polymerase is (exo–) *Pyrococcus furiosus* DNA polymerase.

23. A composition according to claim 17, wherein the second DNA polymerase is (exo–) *Pyrococcus* GB-D DNA polymerase.

24. A composition according to claim 18, wherein the second DNA polymerase is *Thermus aquaticus* DNA polymerase.

25. A composition according to claim 18, wherein the second DNA polymerase is (exo–) *Thermococcus litoralis* DNA polymerase.

26. A composition according to claim 18, wherein the second DNA polymerase is (exo–) *Pyrococcus furiosus* DNA polymerase.

27. A composition according to claim 18, wherein the second DNA polymerase is (exo–) *Pyrococcus* GB-D DNA polymerase.

28. A composition according to claim 19, wherein the second DNA polymerase is *Thermus aquaticus* DNA polymerase.

29. A composition according to claim 19, wherein the second DNA polymerase is (exo–) *Thermococcus litoralis* DNA polymerase.

30. A composition according to claim 19, wherein the second DNA polymerase is (exo–) *Pyrococcus furiosus* DNA polymerase.

31. A composition according to claim 19, wherein the second DNA polymerase is (exo–) *Pyrococcus* GB-D DNA polymerase.

32. A method of synthesizing a polynucleotide sequence, said method comprising mixing a composition with a synthesis primer and a synthesis template, said composition comprising
(a) a first DNA polymerase possessing 3'–5' exonuclease activity, wherein said first polymerase is thermostable, and
(b) a second DNA polymerase, wherein said second polymerase substantially lacks 3'–5' exonuclease activity and is thermostable;
wherein both the first DNA polymerase and the second DNA polymerase retain at least 50 percent of their specific activity after exposure to a temperature of 80 degrees Celsius for a period of 20 minutes.

33. A method according to claim 32, wherein said first DNA polymerase is selected from the group consisting of *Pyrococcus furiosus* DNA polymerase, *Thermotoga maritima* DNA polymerase, *Thermococcus litoralis* DNA polymerase, and *Pyrococcus* GB-D DNA polymerase.

34. A method according to claim 33, wherein said first DNA polymerase is *Pyrococcus furiosus* DNA polymerase.

35. A method according to claim 32, wherein the second DNA polymerase is selected from the group consisting of *Thermus aquaticus* DNA polymerase, (exo–) *Thermococcus litoralis* DNA polymerase, (exo–) *Pyrococcus furiosus* DNA polymerase, and (exo–) *Pyrococcus* GB-D DNA polymerase.

36. A method according to claim 32, wherein said second DNA polymerase is *Thermus aquaticus* DNA polymerase.

37. A method according to claim 33, wherein the second DNA polymerase is selected from the group consisting of *Thermus aquaticus* DNA polymerase, (exo–) *Thermococcus litoralis* DNA polymerase, (exo–) *Pyrococcus furiosus* DNA polymerase, and (exo–) *Pyrococcus* GB-D DNA polymerase.

38. A method according to claim 34, wherein said second DNA polymerase is *Thermus aquaticus* DNA polymerase.

39. A method according to claim 32, wherein the first DNA polymerase is selected from the group consisting of *Pyrococcus furiosus* DNA polymerase, *Thermococcus litoralis* DNA polymerase, and *Pyrococcus* GB-D DNA polymerase.

\* \* \* \* \*